United States Patent
Kasuga et al.

[11] Patent Number: 6,133,502
[45] Date of Patent: Oct. 17, 2000

[54] MONOCYTE CHEMOATTRACTANT PROTEIN AND ITS RECEPTOR TRANSGENIC ANIMAL

[75] Inventors: Hisao Kasuga, Toyonaka; Takahito Kitayoshi, Suita; Masami Isaka, Osaka, all of Japan

[73] Assignee: Takeda Chemical Industries, Ltd., Osaka, Japan

[21] Appl. No.: 09/037,327

[22] Filed: Mar. 9, 1998

[30] Foreign Application Priority Data

Mar. 10, 1997 [JP] Japan ................................. 9-055129

[51] Int. Cl.$^7$ ........................... A01K 67/00; C12N 15/63
[52] U.S. Cl. ............................... 800/14; 800/8; 800/13; 800/18; 435/172.3; 435/320.1
[58] Field of Search ................... 800/2, DIG. 1, 800/8, 18, 14, 13; 435/320.1, 172.3

[56] References Cited

U.S. PATENT DOCUMENTS

| | | | |
|---|---|---|---|
| 4,338,305 | 7/1982 | Corbin | 424/177 |
| 5,817,911 | 10/1998 | Williams et al. | 800/2 |

OTHER PUBLICATIONS

K. Nakamura, et al. *J. Invest. Dermatol.*105: 635 (1995).

M.E. Fuentes, et al. *The Journal of Immunology* 155: 5769 (1995).

B.J. Rutledge, et al. *The Journal of Immunology* 155: 4838 (1995).

Hammer RE, Maika SD, Richardson JA, Tang J, and Taurog JD. Spontaneous inflammatory disease in transgenic rats expressing HLA–B27 and Human beta–2 m:an animal model of HLA–B27–associated human disorders. Cell 63:1099–1112, 1990.

Charreau B, Tesson L, Buscail J, Soulillou J and Anegon I. Analysis of human CD59 tissue expression directed by the CMV–IE–1 promoter in transgenic rats. Transgenic Research 5: 443–450, 1996a.

Gunn MD, Nelken NA, Liao X, and Williams LT. Monocyte chemoattractant protein–1 is sufficient for the chemotaxis of monocytes and lymphocytes in transgenic mice but requires an additional stimulus for inflammatory activation. Journal of Immunology 158: 376–383, 1997.

Nelken NA, Coughlin SR, Gordon D and Wilcox JN. Monocyte chemoattractant protein–1 in human atheromatous plaques. J Clin Invest. 88:1121, 1991.

Yoshimura et al. Molecular cloning of rat moncyte chemoattractant protein–1 (MCP–1) and its expression in rat spleen cells and tumor cell lines. Biochemial Biophysical Research Communicaton. 174:504, 1991.

The stratagene catalog. pp. 26 and 44, 1995.

Wall. Transgenic livestoc: progress and prospects for the future. Theriogenology, vol. 45, pp. 57–68, 1996.

Overbeek, PA. Factors affecting transgenic animal production. "Transgenic animal technology." Pinkert, CA, ed., Academic Press, Inc, 1994.

Kappel, CA, et al. Regulating gene expression in transgenic animals. Current Opinion in Biotechnology, vol. 3, pp. 548–553, 1992.

Mullins and Mullins. Transgenesis in nonmurine species. Hypertension, vol. 22, pp. 630–634, 1993.

(List continued on next page.)

*Primary Examiner*—Brian R. Stanton
*Attorney, Agent, or Firm*—Dike, Bronstein, Roberts & Cushman, LLP; David G. Conlin

[57] ABSTRACT

Provided is a non-human animal in which an exogeneous gene, a mutant gene thereof of a monocyte chemoattractant protein and/or a receptor thereof is introduced. The present transgenic animals can be utilized as a pathologic model animal for heart diseases, respiratory diseases, joint diseases, kidney diseases, arteriosclerosis, psoriasis, hyperlipidemia, allergic diseases, bone diseases, blood diseases, cerebrovascular disorders, traumatic cerebral disorders, infections diseases, demantia or chroric inflammatory diseases etc. Thus, it is possible to elucidate the mechanism of pathogenesis of these diseases, to determine therapies, and to screen for candidate compounds for the purpose of research and development of therapeutic drugs.

2 Claims, 14 Drawing Sheets

OTHER PUBLICATIONS

Strojek, RM. The use of transgenic animal techniques for livestock improvement. Genetic engineering: principles and methods. Plenum Press, vol. 10, pp. 221–246,1988.

Robl, JM. Production of transgenic rats and rabbits. "Transgenic animal technology." Pinkert, CA, ed., Academic Press, Inc., pp. 265–270, 1994.

Heideman, J. Trangenic rats: a discussion. Biotechnology, vol. 16, pp. 325–332, 1991.

Opavsky, MA, et al. Effects of luteinizing hormone on superovulatory and steroidogenic responses of rat ovaries to infusion with FSH. Biol. Reprod., vol. 41, pp. 15–25, 1989.

Charreaum, B. Transgenesis in rats: technical aspects and models. Transgenic research, vol. 5, pp. 223–234, Jul. 1996.

Paul, M. Transgenic rats: new experimental models for the study of candidate genes in hypertension research. Annual review of physiology, vol. 56, pp. 811–829, 1994.-

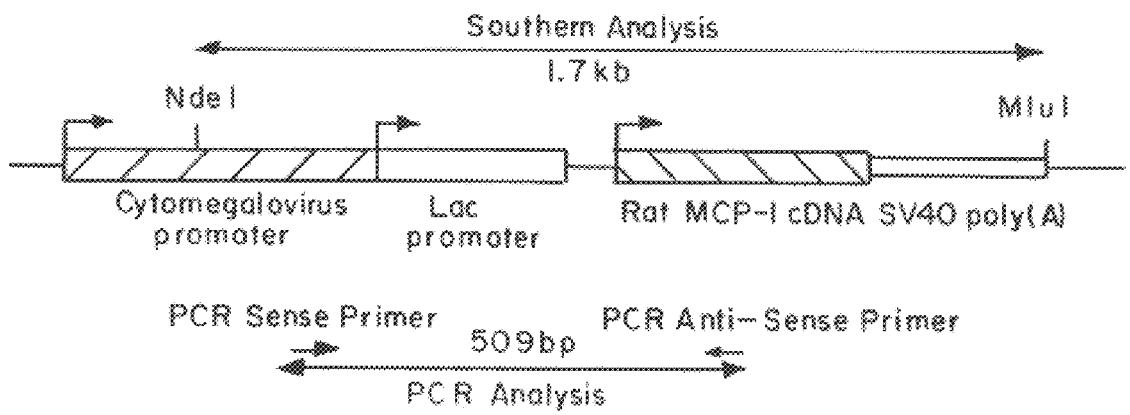
FIG. 2
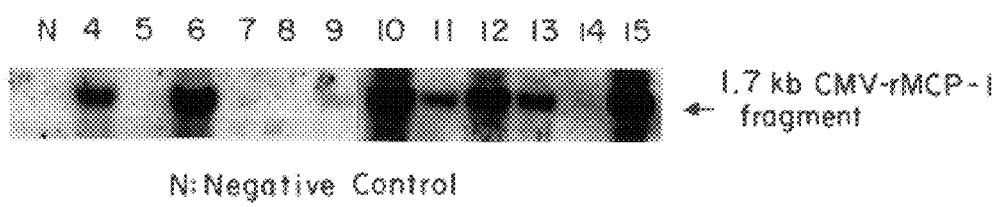
FIG. 3
| Gene | Line | | Birth day | PCR anal. | Southern anal. |
|---|---|---|---|---|---|
| CMV-rMCP-1 | R03056-2 | ♂ | 96.03.28 | + | + (Lane 4) |
| | R03056-3 | ♂ | 96.03.28 | ± | − (Lane 5) |
| | R03073-7 | ♀ | 96.03.30 | + | + (Lane 6) |
| | R03075-6 | ♂ | 96.03.30 | + | − (Lane 7) |
| | R03123-8 | ♂ | 96.04.04 | + | − (Lane 8) |
| | R03124-4 | ♀ | 96.04.04 | + | + (Lane 9) |
| | R03125-4 | ♂ | 96.04.04 | + | + (Lane 10) |
| | R03125-8 | ♀ | 96.04.04 | + | + (Lane 11) |
| | R03142-2 | ♂ | 96.04.06 | + | + (Lane 12) |
| | R03142-12 | ♀ | 96.04.06 | + | + (Lane 13) |
| | R03143-3 | ♀ | 96.04.06 | + | − (Lane 14) |
| | R03143-5 | ♂ | 96.04.06 | + | + (Lane 15) |
FIG. 4

MONOCYTE CHEMOATTRACTANT PROTEIN AND ITS RECEPTOR TRANSGENIC ANIMAL

FIELD OF THE INVENTION

The present invention relates to a transgenic animal in which an exogenous gene of a monocyte chemoattractant protein and/or a receptor thereof is introduced.

BACKGROUND OF THE INVENTION

A transgenic animal is defined as an animal having an exogenous gene introduced into the germinal line of the animal or an ancestor thereof, typically in the initial (usually single-cell) developmental stage.

Wagner et al. (Proc. Nat. Acad. Sc. U.S.A., Vol. 78, p. 5016, 1981) and Stewart et al. (Science, Vol. 217, p. 1046, 1982) described a transgenic mouse containing the human globin gene. Constantini et al. (Nature, Vol. 294, p. 92, 1981) and Lacy et al. (Cell, Vol. 34, p. 343, 1983) described a transgenic mouse containing the rabbit globin gene. McKnight et al. (Cell, Vol. 34, p. 335, 1983) described a transgenic mouse containing the transferrin gene. Brinstar et al. (Nature, Vol. 306, p. 332, 1983) described a transgenic mouse containing a functionally transfected immunoglobulin gene. Palmiter et al. (Nature, Vol. 300, p. 611, 1982) described a transgenic mouse containing the rat growth hormone gene ligated to a heavy metal-induced metallothionein promoter sequence. Palmiter et al. (Cell, Vol. 29, p. 701, 1982) described a transgenic mouse containing the thymidine kinase gene ligated to a metallothionein promoter sequence. Palmiter et al. (Science, Vol. 222, p. 809, 1983) described a transgenic mouse containing the human growth hormone gene ligated to a metallothionein promoter sequence.

Matsushima et al. (J. Exp. Med., Vol. 169, p. 1485, 1987) described a polypeptide factor showing chemotaxis for neutrophils referred to a interleukin 8 (generally abbreviated IL-8); Since then, a large number of genes that are specifically expressed in similarly activated lymphocytes etc. have been cloned. These factors called chemokines, which mean cytokines showing chemotaxis for a particular form of leukocytes.

The monocyte chemotactic and activating factor (which is now called MCP-1), a chemokine, was for the first time isolated from a human monocytic leukemia cell line (THP-1) by Matsushima et al. (J. Exp. Med., Vol. 169, p. 1485, 1989), followed by successful cloning of the cDNA thereof. Separately, Yoshimura et al. (J. Exp. Med., Vol. 169, p. 1449, 1989) isolated the monocyte chemotactic and activating factor from a human glioma cell line (U-105MG) and subsequently succeeded in cloning the cDNA thereof. Matsushima et al. and Yoshimura et al. designated this factor as the monocyte chemotactic and activating factor (generally abbreviated MCAF) and monocyte chemoattractant protein (generally abbreviated MCP-1), respectively. This factor is also called MCAF/MCP-1 to represent both designations.

MCAF/MCP-1 is a basic heparin-binding polypeptide that belongs to a subfamily of C-C chemokines (also referred to as β chemokines), which are characterized by the presence of 4 cysteins, including 2 mutually adjoining cysteins, in the molecular structure thereof. Regarding the genetic structure thereof, it is known that the propeptide moiety, consisting of 23 amino acids at the amino acid terminus (generally abbreviated N-terminus), is cleaved after translation, resulting in the formation and secretion of a mature protein consisting of 76 amino acids. It is about 8.7 kD in size and is rich in the basic amino acids lysine and arginine having 2 S-S bonds; according to Zhang et al. (Mol. Cell Biol., Vol. 15, p. 4851, 1995), its biological activity results from dimerization.

A mouse gene previously known as the JE gene, reported by Rollins, B. J. et al. (Proc. Nat. Acad. Sc. U.S.A., Vol. 85, p. 3738, 1988), was reestablished as the cDNA homologous to the human monocyte chemotactic and activating factor gene. Yoshimura et al. (Biochem. Biophys. Res. Commun., Vol. 174, p. 504, 1991) reported on the homologous cDNA in the rat.

The monocyte chemotactic and activating factor gene is located on the human 17th chromosome or the mouse 4th chromosome, it consists of 3 exons and 2 introns, includes a transcription factor-binding site 5' upstream of AP-1, AP-2, NF-$_K$B, NF-IL6 etc. and the ATTTA motif in the 3' non-translational region. Also, base substitutions in its cDNA are known.

The monocyte chemotactic and activating factor is known to be produced upon stimulation by TNF-α or lipopolysaccharide (generally abbreviated LPS). Currently known biological activities of the monocyte chemotactic and activating factor include (1) chemotaxis promotion, (2) lysosome enzyme production and release, (3) IL-1 and IL-6 production promotion, (4) antitumor activity enhancement, and (5) adhesive molecule (CD11b/c) expression promotion. The monocyte chemotactic and activating factor is also known to have biological activities on basophils, including (1) chemotaxis promotion, (2) histamine release promotion, and (3) degranulation. Furthermore, the monocyte chemotactic and activating factor is known to serve as a T-cell chemotactic factor; Duboi, P. M. et al. (J. Immunol., Vol. 156, p. 1356, 1996) reported that the monocyte chemotactic and activating factor causes MAP kinase activation; del Pozo, M. A. et al. (J. Cell Biol., Vol. 131, p. 495, 1995) reported that the monocyte chemotactic and activating factor, along with the RANTES (regulated upon activation, normal T expressed and presumably secreted) C-C chemokine, induces T-cell process formation and cell surface CAM3 re-distribution; the signal transmission mechanism of the monocyte chemotactic and activating factor is also being extensively studied.

In addition, there are 13,000 monocyte chemotactic and activating factor receptors on the monocyte, which receptors have an affinity of 0.26 nM Kd value; the cDNA of this receptor was cloned by Charo et al. (Proc. Nat. Acad. Sc. U.S.A., Vol. 91, p. 2752, 1994). Structural analysis demonstrated that this cDNA is a G protein-binding type receptor having 7 transmembrane sites and that 2 receptor isoforms occur due to alternative splicing at the carboxyl terminus. These isoforms are C-C chemokine receptor type 2A (generally called CCCK2A, CCR2A or CCR2) and type 2B (generally called CCCK2B, CCR2B or CCR2). These receptors are known to possess affinity for monocyte chemoattractant protein-2 (generally called MCP-2), monocyte chemoattractant protein-3 (generally called MCP-3) monocyte chemoattractant protein-4 and monocyte chemoattractant protein-5 (generally called MCP-4 and MCP-5) (Luster, A. D. The New England Journal of Medicine, Vol., 338, page 436, 1998) as well, and showed 51% homology to previously cloned C-C chemokine receptor type 1 (generally called CCCK1, CCR$_1$ or CCR1).

Monteclaro et al. (The Journal of Biological Chemistry, Vol. 272, p. 23186, 1996) conducted a ligand-binding experiment and identified a 35-amino terminus as an essential region with high binding capability.

Using cells transformed with the gene for said receptor, it has been shown that transfection with said gene increases calcium concentration with dependency on MCP-1 concentration and promote MAP kinase activation. Also, induction of formation of T cell projections and re-distribution of the cell surface adhesion molecule ICAM-3 was reported by del Pozo et al. (Journal of Cell Biology, Vol. 131, p. 495, 1995.

Frade et al. (The Journal of Clinical Investigation, Vol. 100, p. 497, 1997) examined the effects of MCP-1 and monoclonal antibody against said receptor on the replication of the human immunodeficiency virus type 1 (generally called HIV-1) in monocytes, and found that HIV-1 was suppressed by the monoclonal antibody against the receptor's amino terminus, as well as by MCP-1. They suggested that said receptor and C-C chemokine receptor type 5 (generally called CCCK5, $CCR_5$ or CCR5) both act as common receptors in M.T tropic HIV-1 infection.

Smith et al. (Science, Vol. 277, p. 959, 1997) demonstrated that a variation of the 64th amino acid, valine, in said receptor to isoleucine does not affect HIV-1 infection but the progression of acquired immunodeficiency syndrome (generally called AIDS) is delayed by 2 to 4 years in those with HIV-1 infection in comparison to other patients. In addition, they showed that 28–29% of long survivors with AIDS have a deficiency of C-C chemokine receptor type 5 or a variation in the 64th amino acid.

However, Michael et al. (Nature Medicine, Vol. 3, p. 1160, 1997) showed that amino acid variation in said receptor does not change HIV-1 growth in plasma, suggesting that the variation does not affect the progression of AIDS.

The mouse monocyte chemotactic and activating factor receptor (generally called JE receptor) was for the first time cloned by Boring et al. (Journal of Biological Chemistry, Vol. 271, p. 7551). The JE receptor, which encodes 373 amino acids, was suggested as having 7 transmembrane sites, judging from its hydrophobicity, and showed 75% homology to the human monocyte chemotactic and activating factor receptor. Its carboxyl terminus, in particular, showed 81% homology to C-C chemokine receptor type 2B.

Regarding a monocyte chemotactic and activating factor receptor, the same authors (Boring et al., The Journal of Clinical Investigation, Vol. 100, p. 2552, 1997) created a mouse lacking the gene therefor. Although that homodeficient mouse grew normally, monocyte chemotactic response to a monocyte chemotactic and activating factor (MCP-1) was reduced. In addition, in comparison with normal animals, that mouse had decreased granulocyte size due to dramatic reduction in interferon γ in lymph nodes, demonstrating that said gene plays an important role in the sensitivity and production of Th-1 type cytokines.

Although there are no known homologues of said receptor other than in the mouse, Bonini et al. (DNA and Cell Biology, Vol. 16, p. 1249, 1997) cloned a receptor (CCR10) having high bindability to human MCP-1 and MCP-3. The same authors (Bonini et al., DNA and Cell Biology, Vol. 16, p. 1023, 1997) cloned a receptor (rCCR10rR) having high bindability to human MCP-1 and MIP-1β in the rat. For this rCCR10rR, expression at the RNA level was noted in the heart, brain, spleen, lungs, liver and muscles.

Although 2 other receptors are known to possess affinity for monocyte chemotactic and activating factors, i.e., C-C chemokine receptor type 4 (generally called CCCK4) and Duffy antigen/chemokine receptor (generally called DARC), the differences in their ligand-receptor interaction remain unknown.

A correlation with expression of monocyte chemotactic and activating factors has been reported in such diseases as tuberculous pleurisy, fibroid lung, rheumatoid arthritis, glomerular nephritis, IgA nephropathy, arteriosclerosis and psoriasis. In hyperlipidemia and arteriosclerosis, expression of monocyte chemotactic and activating factors in arterial medial smooth muscle cells, intimal macrophages and vascular endothelial cells has been reported, with a report concluding that monocyte chemotactic and activating factors play a roll in the suppression of vascular smooth muscle cell proliferation.

Expression of monocyte chemotactic and activating factor mRNA is seen in the cardiac muscle of chronic heart failure patients (Seino et al., Cytokine, Vol. 7, p. 301, 1995); expression of monocyte chemotactic and activating factor mRNA is also known to increase in the blood of acute heart failure patients as well. Matsushima, K. et al. (FASEB J., Vol. 10, p. 1418, 1996) showed that the MCP-1 neutralization antibody improves the pathologic state in a rat acute glomerular nephritis model. Association with infectious diseases, allergic diseases, bone diseases, sepsis, chronic gingivitis, dementia, traumatic cerebral disorders (Glabinski, A. R. et al., Journal of Immunology, Vol. 156, p. 4363, 1996) etc. has also been suggested.

Regarding monocyte chemotactic and activating factor transgenic mice, the following reports are available: Nakamura, K. et al. (J. Invest. Dermatol., Vol. 105, p. 635, 1995) reported that monocyte infiltration was observed histologically in a mouse transfected with the JE gene, that showed expression of the gene in the skin. Rutledge, B. et al. (Journal of Immunology, Vol. 155, p. 4838, 1995) reported that the JE gene-transformed mouse is highly sensitive to Listeria and Mycobacterium. Fuentes, M. E. et al. (Journal of Immunology, Vol. 155, p. 5769, 1995) reported that the number of monocytes increased in mice transfected with the JE gene, and showed expression of the gene in the thymus and brain. In addition, Grewal, I. S. et al. (Journal of Immunology, Vol. 159, p. 401, 1997), who worked in a group in cooperation with Fuentes et al., created a JE gene-transformed mouse showing expression of that gene in islets, and also created a mouse transformed with both genes by crossing with the mouse of Fuentes et al. However, almost no cell infiltration was observed in islets.

Iwabuchi et al. (Proceedings of the 1995 Assembly of the Japanese Society for Immunology) created a human monocyte chemotactic and activating factor transgenic mouse, confirmed expression of the gene in the thymus, spleen, liver and testis, and detected the human monocyte chemotactic and activating factor at a blood concentration of 11,492 pg/ml. Gunn, M. D. et al. (Journal of Immunology, Vol. 158, p. 376, 1997) reported that human monocyte chemotactic and activating factor transgenic animals had that factor expressed in type II pulmonary alveolar epithelium and bronchial epithelium, with increased counts of leukocytes, monocytes and T cells in pulmonary alveoli.

There have been no reports on animals transformed with a gene for a monocyte chemotactic and activating factor receptor or those transformed with both genes for a monocyte chemotactic and activating factor and a monocyte chemotactic and activating factor receptor.

SUMMARY OF THE INVENTION

Therefore, successful creation of a transgenic animal having DNA incorporating a monocyte chemoattractant protein gene, its receptor gene or a mutant gene thereof, that can serve as a pathologic model, would enable the elucidation of monocyte chemoattractant protein function, the elucidation of the mechanism of onset of inflammation and determination of clinical therapies in heart diseases (e.g., myocardial infarction, acute heart failure, chronic heart failure, myocarditis), infectious diseases (e.g., acquired immunodeficiency syndrome), allergic diseases (e.g., asthma, allergic rhinitis, atopic dermatitis), hyperlipidemia, arteriosclerosis, joint diseases (e.g., articular rheumatism, osteoarthritis), bone diseases (e.g., osteoporosis, rickets, osteomalacia, hypocalcemia), kidney diseases (e.g., renal insufficiency, glomerular nephritis, IgA nephropathy), sarcoidosis, sepsis, respiratory diseases (e.g., fibrotic lung, pneumonia), chronic inflammatory diseases (e.g., chronic gingivitis), cerebrovascular disorders, dementia, traumatic cerebral disorders etc., supply of cells showing high expression of a particular gene, research into ligand binding of monocyte chemoattractant protein receptors, research into interaction with other chemokines, etc. Also, using a vector containing an exogenous monocyte chemoattractant protein gene, and capable of expressing said gene in a mammal, gene therapy for diseases associated with monocyte chemoattractant protein gene deficiency is enabled.

Moreover, succeeding in creating a transgenic non-human mammal having DNA incorporating a human monocyte chemoattractant protein gene and a corresponding human receptor gene would enable the functional elucidation of monocyte activating factors at the human receptor level using model animals for the above-mentioned diseases, and facilitate the development and research of clinical therapies and therapeutic drugs.

In an attempt to resolve the above problems, the present inventors made extensive investigation, and succeeded in preparing an exogenous monocyte chemoattractant protein transgenic animal having DNA incorporating an exogenous monocyte chemoattractant protein gene, the corresponding receptor gene, or a mutant gene thereof. The inventors made further investigation based on this success, and developed the present invention.

Accordingly, the present invention provides:
(1) a non-human mammal which has a DNA incorporating one or more genes selected from exogenous genes, or mutant genes thereof, of proteins belonging to monocyte chemoattractant protein family and receptors thereof, excluding a transgenic mouse having a DNA into which an exogenous gene of a human or mouse monocyte chemoattractant protein-1 is incorporated,
(2) a non-human mammal according to paragraph (1), which is a rabbit, a dog, a cat, a guinea pig, a hamster, a rat, a mouse, a sheep, a cow or a horse,
(3) a non-human mammal according to paragraph (1), which is a rat,
(4) a non-human mammal according to paragraph (1), wherein the protein belonging to monocyte chemoattractant protein family and/or the receptor thereof is a protein which is capable of binding to C-C chemokine receptor and has monocyte chemoattractant activity and/or a receptor thereof.
(5) a non-human mammal according to paragraph (1), wherein the protein belonging to monocyte chemoattractant protein family and/or the receptor thereof is monocyte chemoattractant protein-1 (MCP-1), monocyte chemoattractant protein-2 (MCP-2), monocyte chemoattractant protein-3 (MCP-3), monocyte chemoattractant protein-4 (MCP-4), monocyte chemoattractant protein-5 (MCP-5), and/or receptors thereof.
(6) a non-human mammal according to paragraph (1), wherein the exogenous gene is a gene of monocyte chemoattractant protein-1 and/or a gene of monocyte chemoattractant protein-1 receptor,
(7) a non-human mammal which has a DNA incorporating one or more of the following exogenous genes encoding proteins belonging to monocyte chemoattractant protein family and receptors thereof, or mutant genes thereof, downstream from a cytomegalovirus promoter,
(8) a non-human mammal according to paragraph (7), wherein the exogenous gene is a gene encoding a rat or human monocyte chemoattractant protein and/or a receptor thereof,
(9) a vector which has a DNA segment encoding one or more the following exogenous genes encoding proteins belonging to monocyte chemoattractant protein family and receptors thereof, or mutant gene thereof, wherein the vector is used for expressing the gene(s) in a mammal, excluding the vector which has an exogenous gene encoding a human or mouse monocyte chemoattractant protein-1 and used for expression in a mouse,
(10) a vector which has one or more of the following exogenous genes encoding proteins belonging to monocyte chemoattractant protein family and receptors thereof, or mutant genes thereof downstream from a cytomegalovirus promotor and used for expression in a mammal,
(11) a vector according to paragraph (10), wherein the exogenous gene is a gene of a rat or human monocyte chemoattractant protein,
(12) a method for creating a transgenic rat, which comprises administering follicle stimulating hormone in an amount of about 20 to 50 IU and then lutenizing hormone in an amount of about 0 to 10 IU per individual to a female rat and mating the thus treated female rat with a male rat,
(13) a method for creating a transgenic rat, which comprises (i) administering lutenizing hormone releasing hormone or a homologue thereof to a female rat, (ii) mating the female rat with a male rat to obtain a pseudopregnant rat, and (iii) allowing the pseudopregnant rat to have an exogenous gene transformed-fertilized egg implanted, and
(14) a method according to paragraph (13), wherein the exogenous gene is one or more selected from exogenous genes encoding proteins belonging to monocyte chemoattractant protein family and receptors thereof, or mutant genes thereof.

BRIEF DESCRIPTION OF THE DRAWINGS

FIG. 2 shows the structure of a gene into which rat MCP-1 cDNA is incorporated downstream of a cytomegalovirus promotor, obtained by Example 2.

FIG. 3 shows the result of Southern hybridization (electrophoresis) conducted in Example 2.

FIG. 4 shows introduction analysis of rat MCP-1 cDNA, conducted in Example 2.

Figure 1:
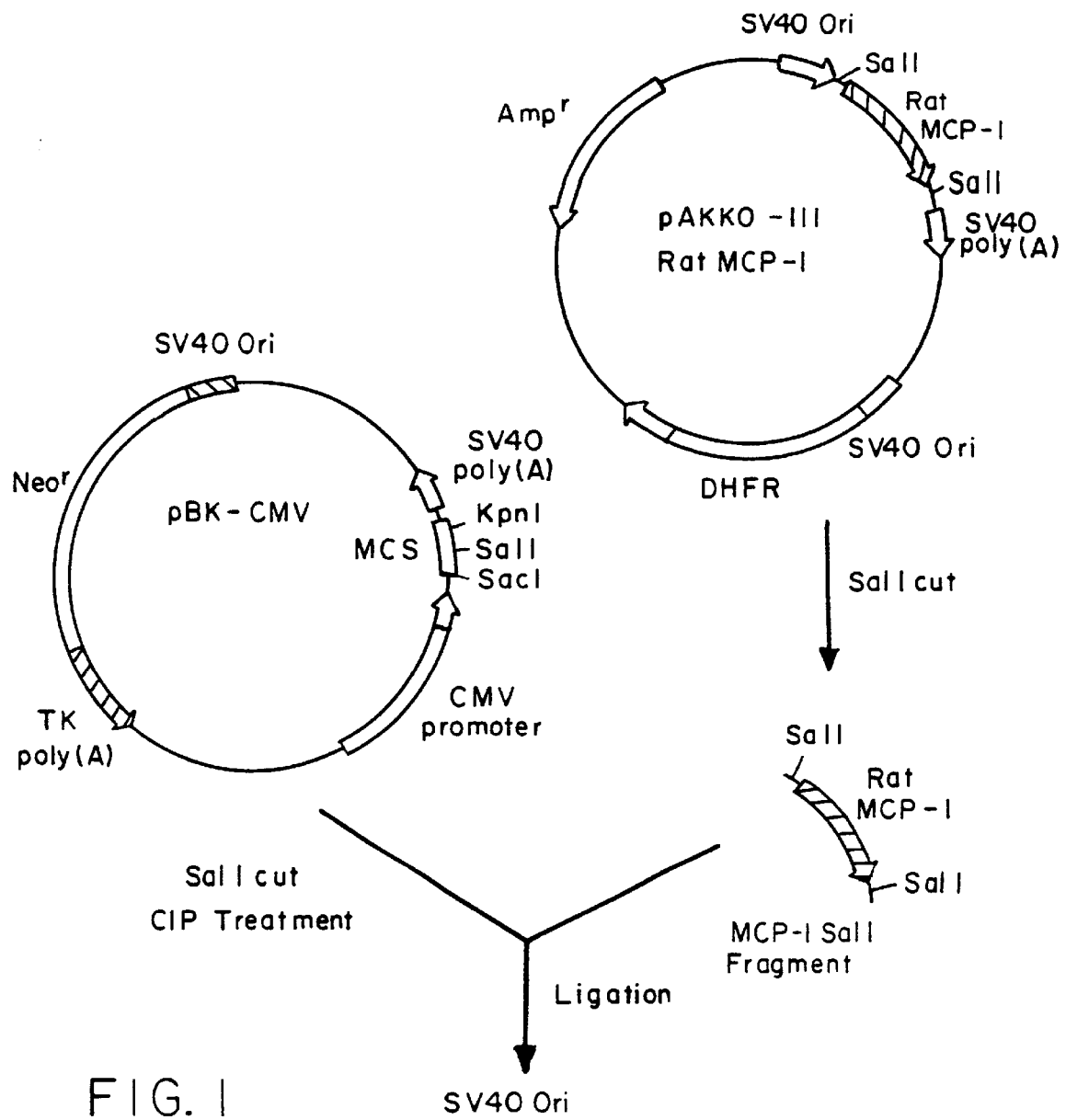
FIG. 1 shows the construction scheme of plasmid pBK-CMV-rat MCP-1 obtained by Example 1.
Figure 1:
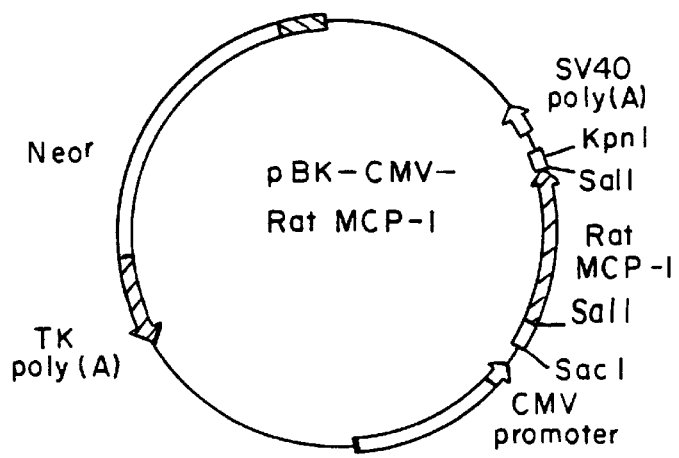
Figure 5:
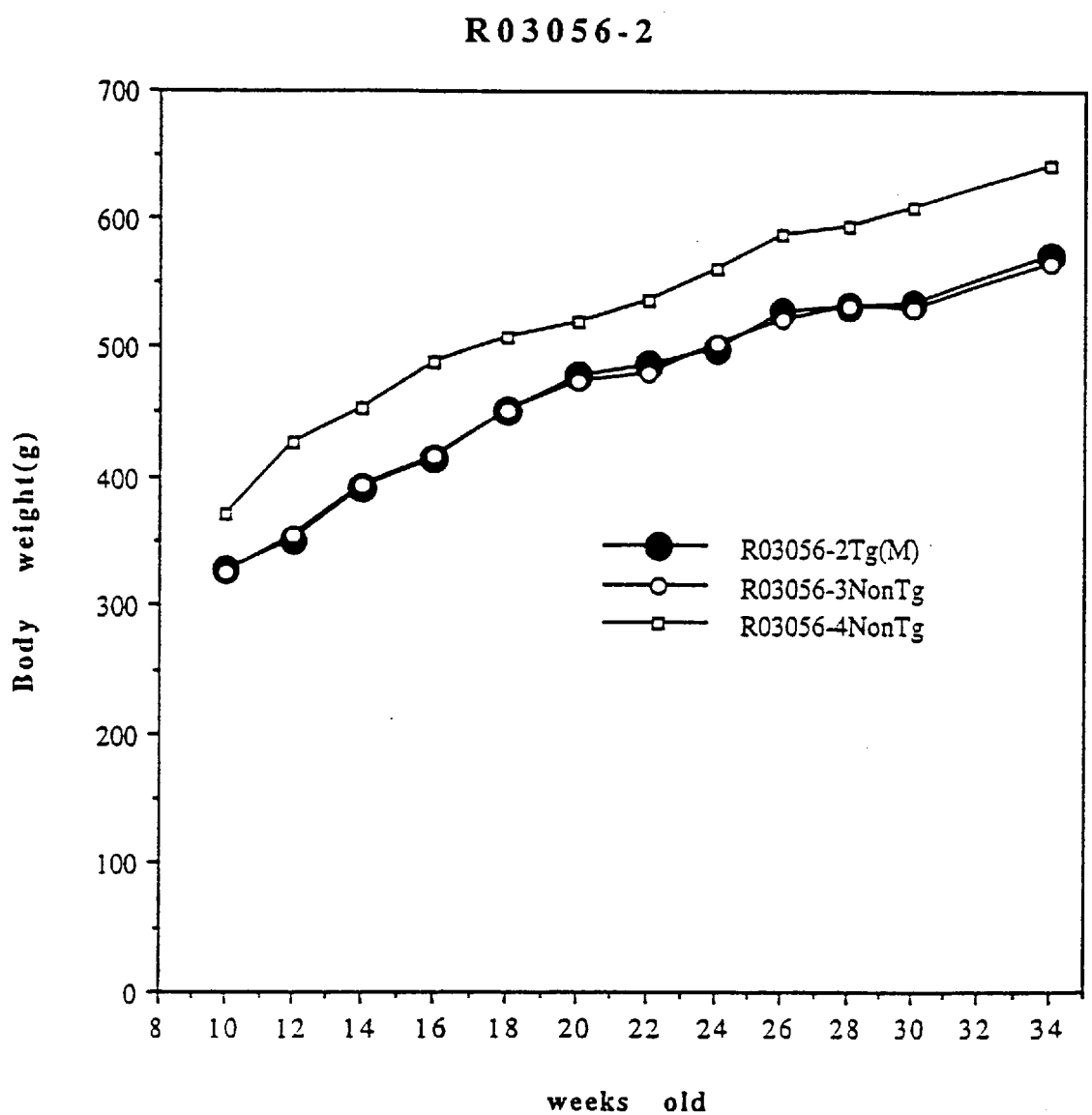
FIG. 5 shows the results of weight body-weighing of the transgenic rat RO3056-2 (male), conducted in Example 3.
Figure 6:
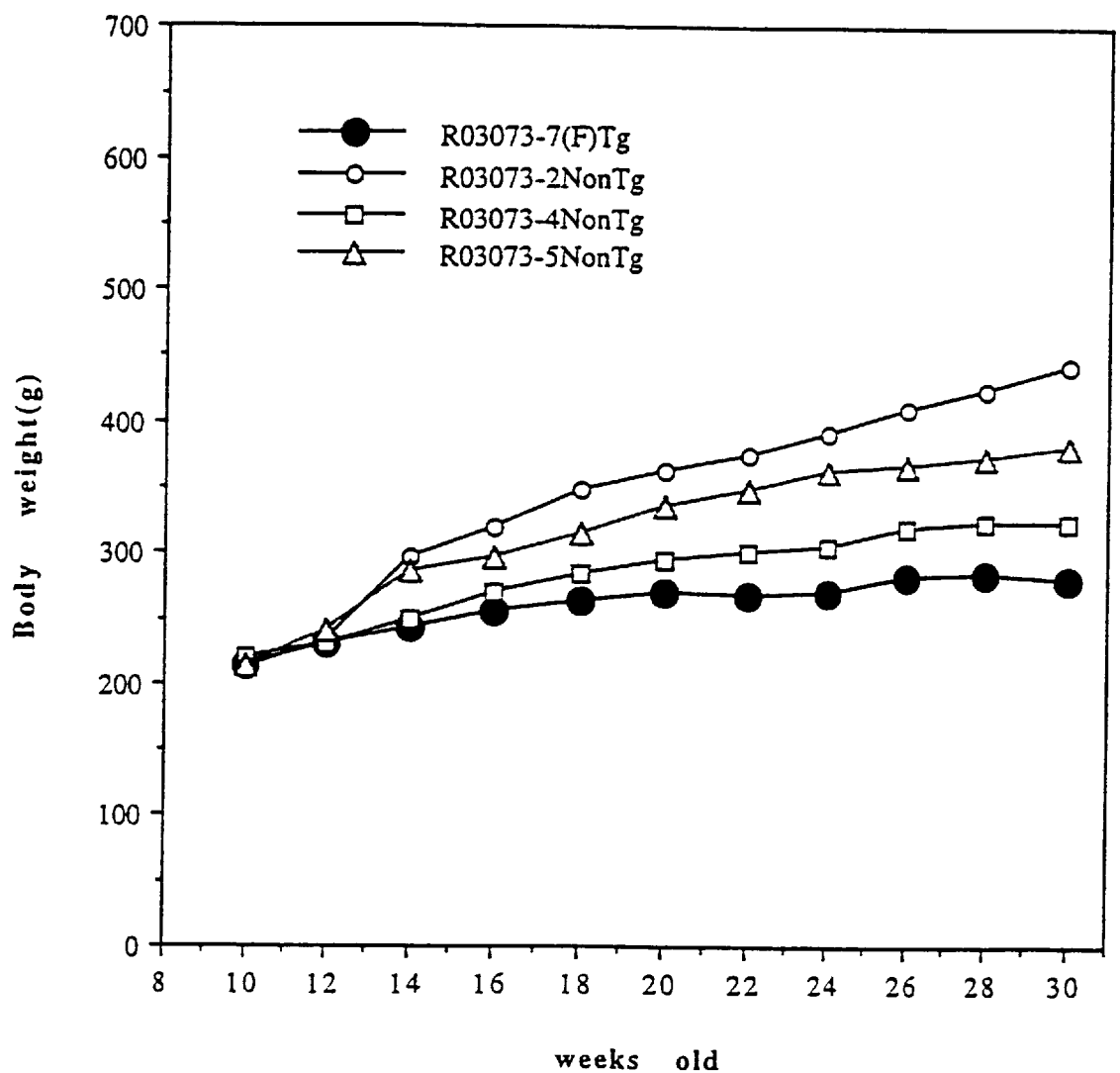
FIG. 6 shows the results of body weight-weighing of the transgenic rat RO3073-7 (female), conducted in Example 3.
Figure 7:
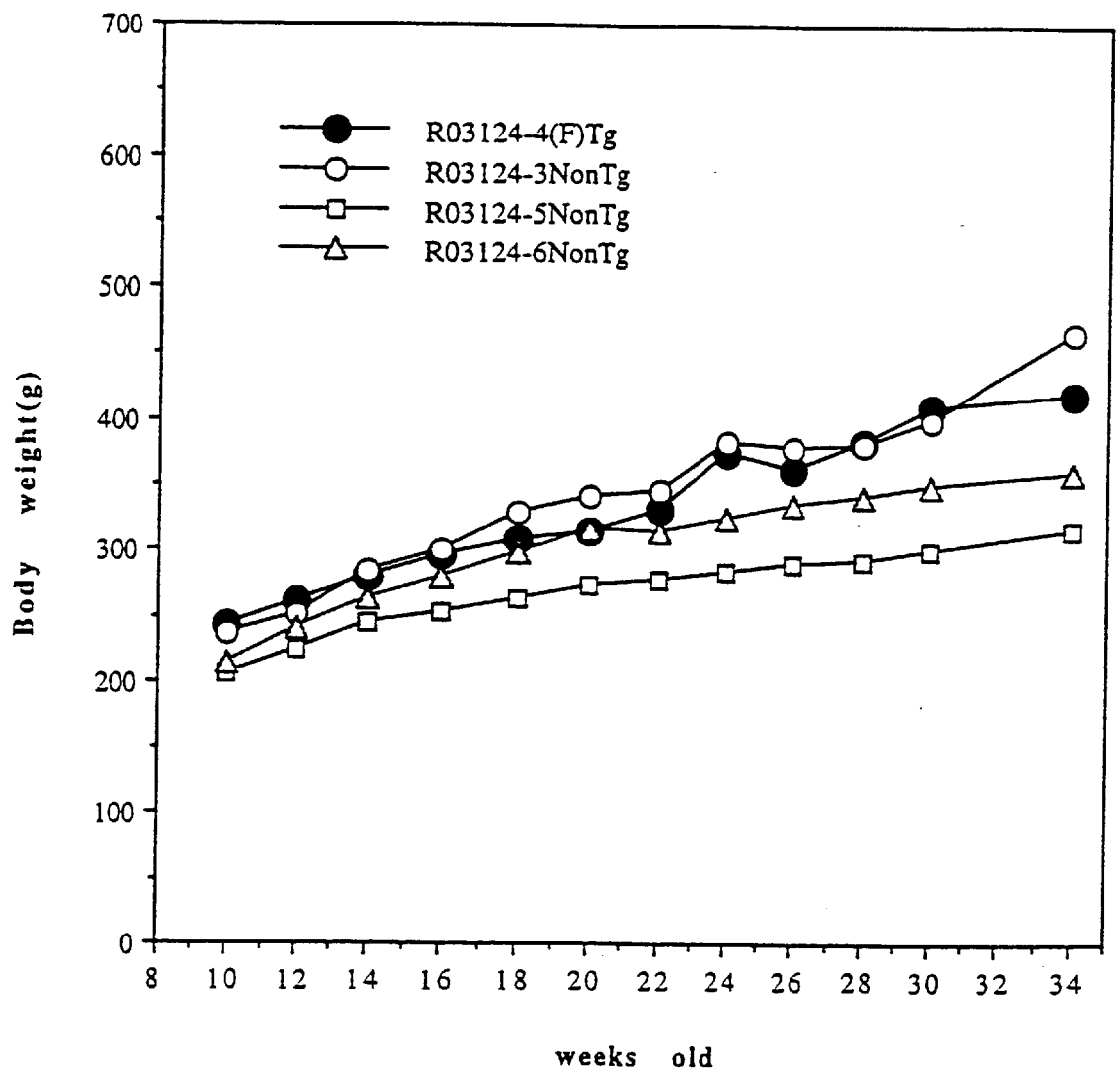
FIG. 7 shows the results of body weight-weighing of the transgenic rat RO3124-4 (female), conducted in Example 3.
Figure 8:
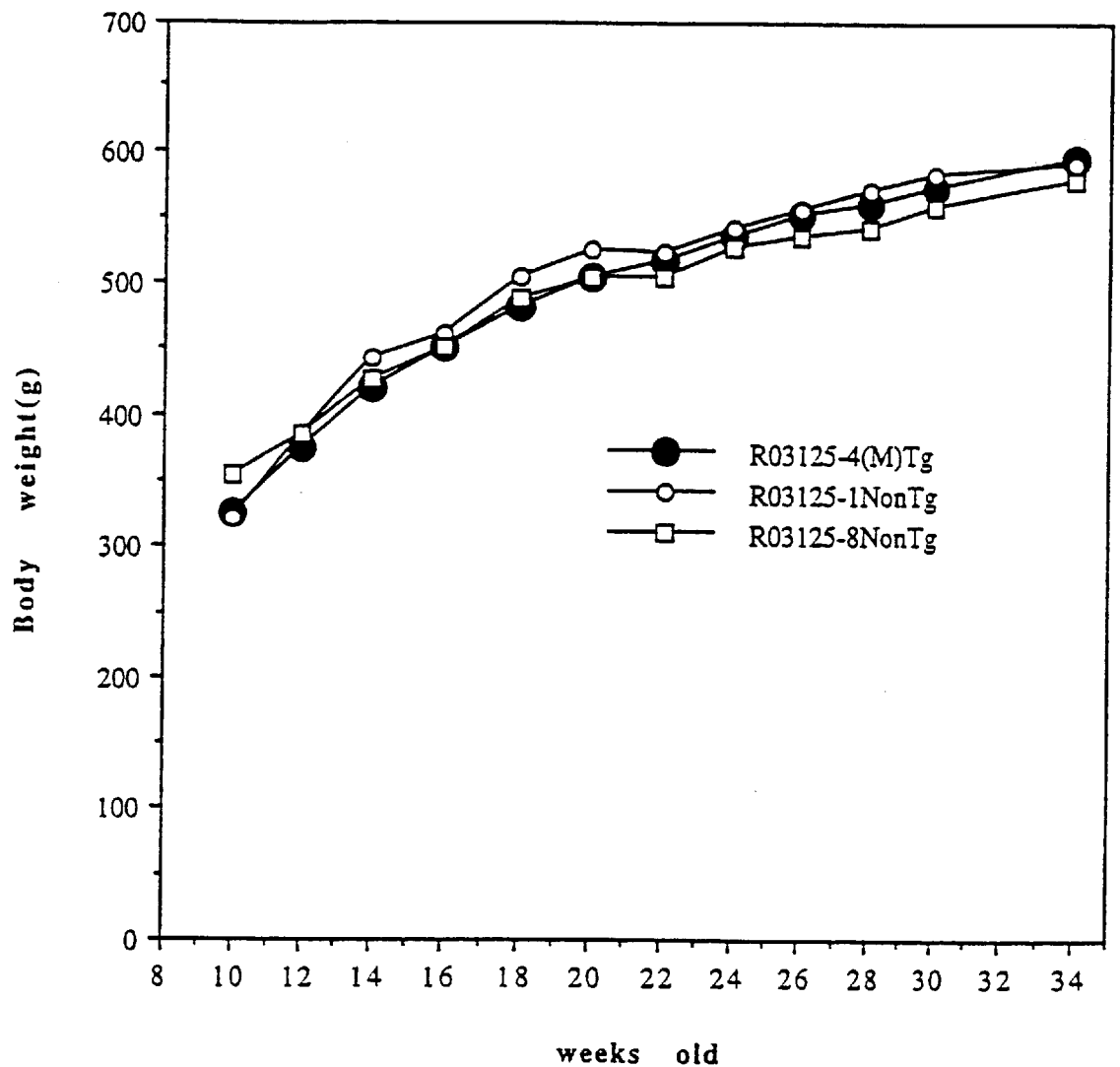
FIG. 8 shows the results of body weight-weighing of the transgenic rat RO03125-4 (male), conducted in Example 3.
Figure 9:
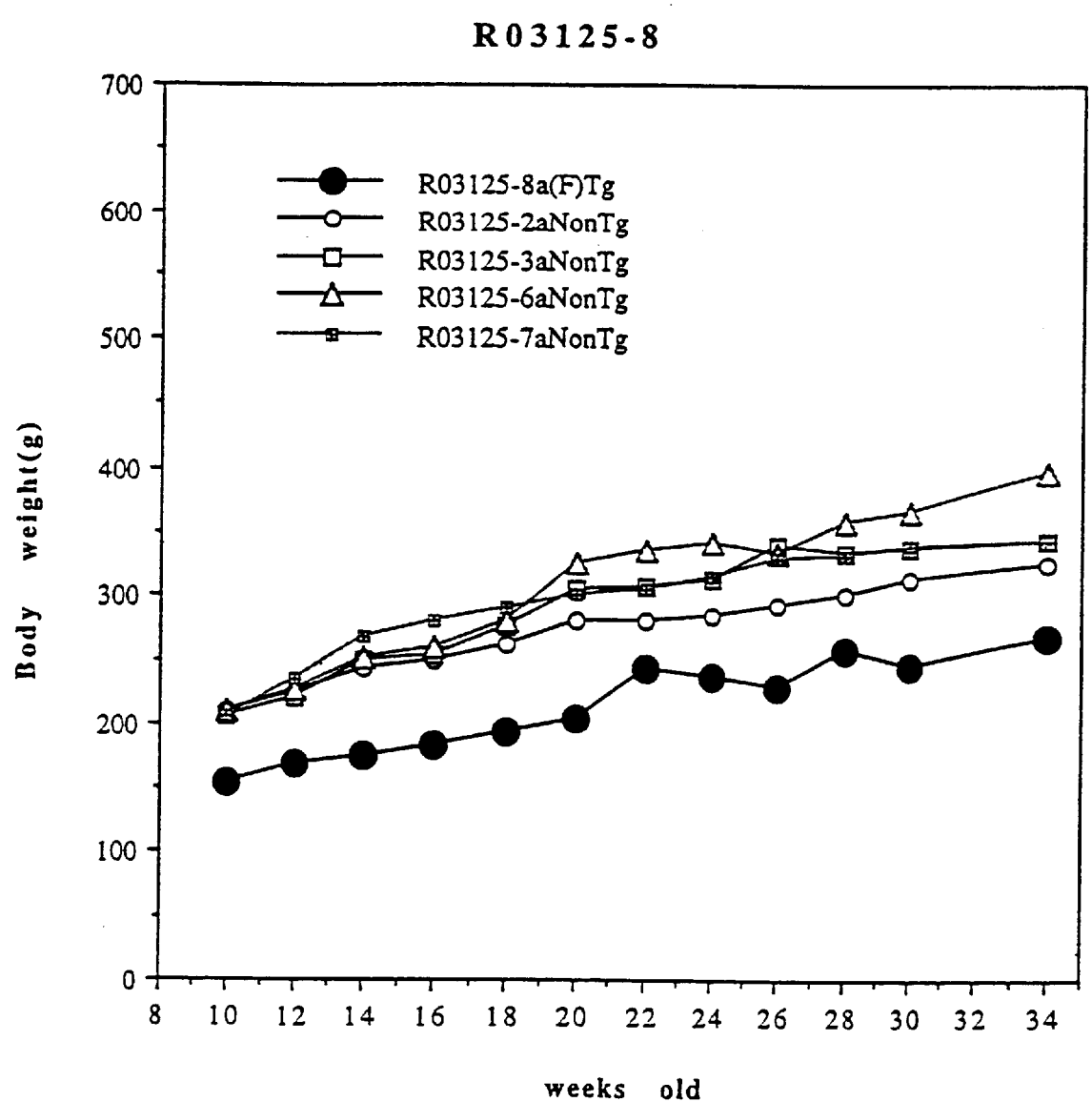
FIG. 9 shows the results of body weight-weighing of the transgenic rat RO3125-8 (female), conducted in Example 3.
Figure 10:
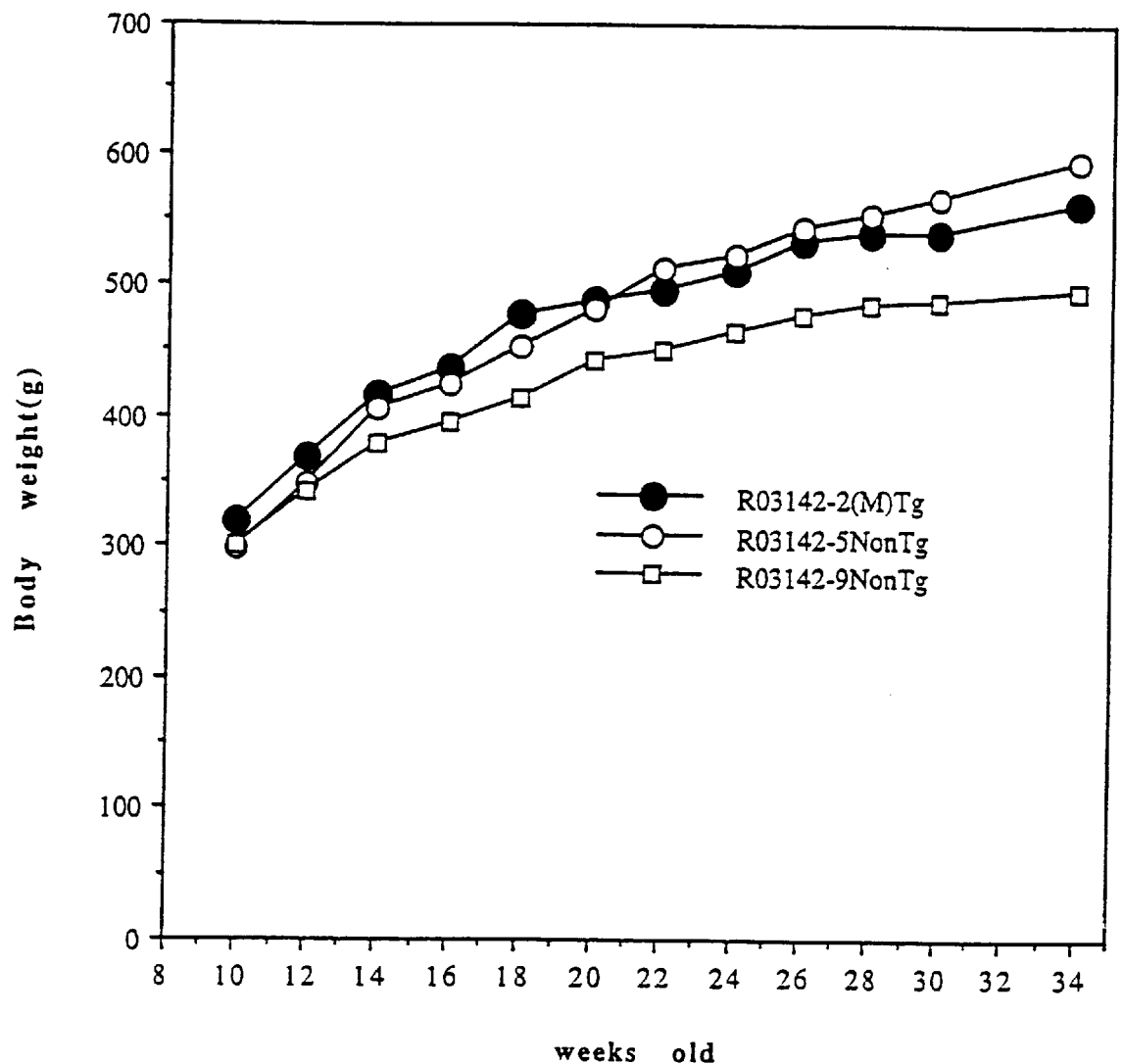
FIG. 10 shows the results of body weight-weighing of the transgenic rat RO3142-2 (female), conducted in Example 3.
Figure 11:
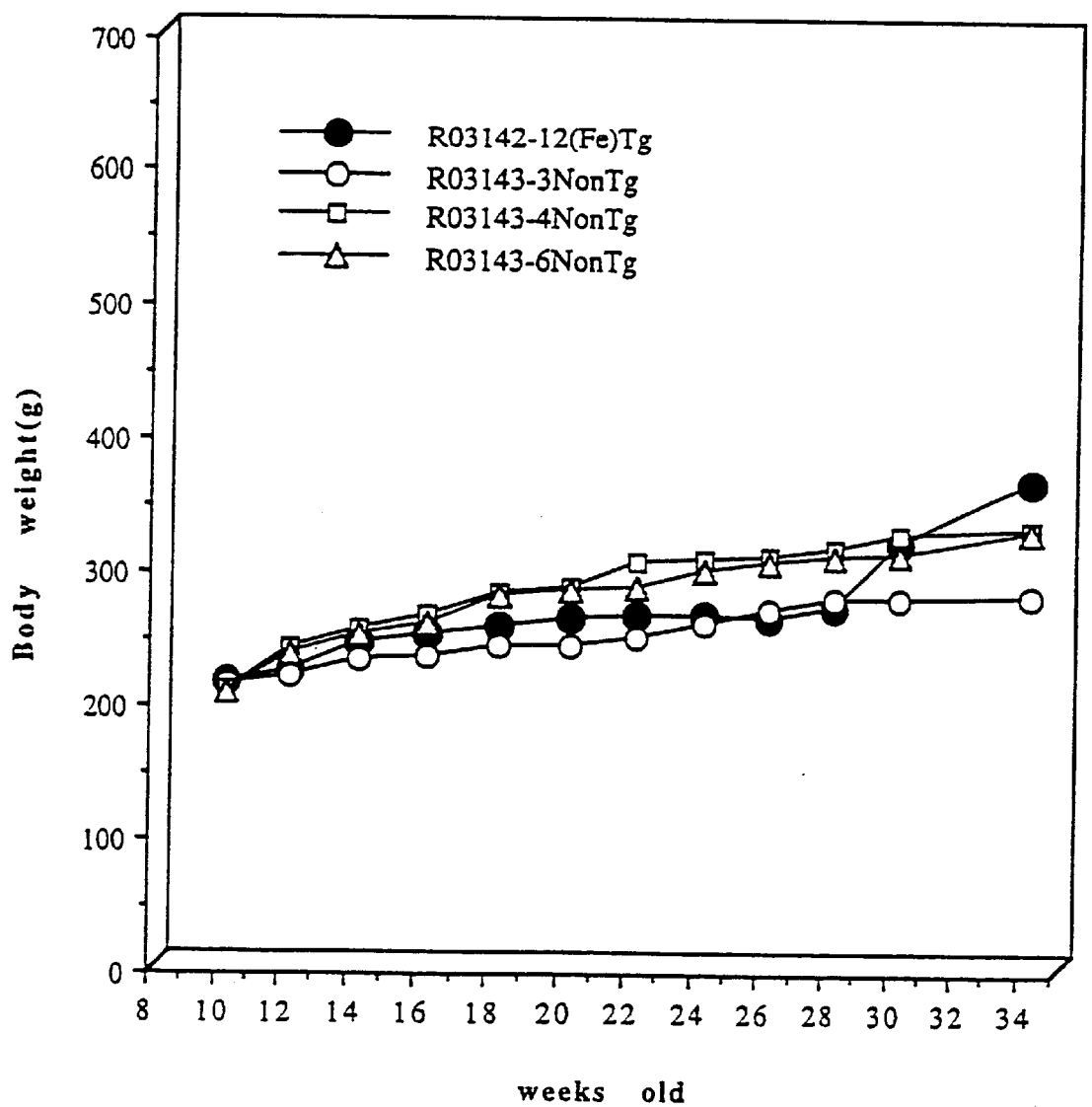
FIG. 11 shows the results of body weight-weighing of the transgenic rat RO3142-12 (female), conducted in Example 3.
Figure 12:
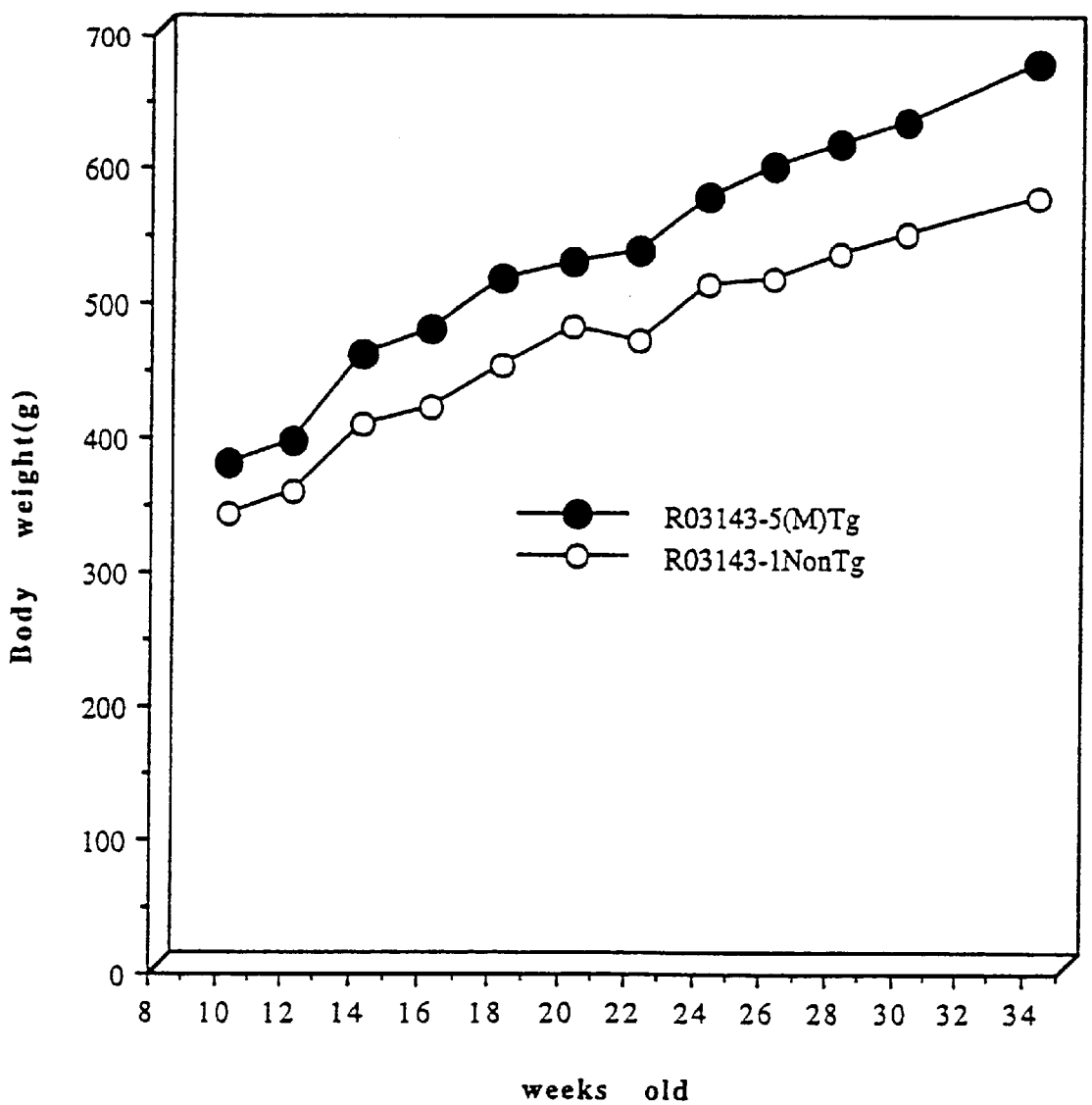
FIG. 12 shows the results of body weight-weighing of the transgenic rat RO3143-5 (female), conducted in Example 3.
Figure 13:
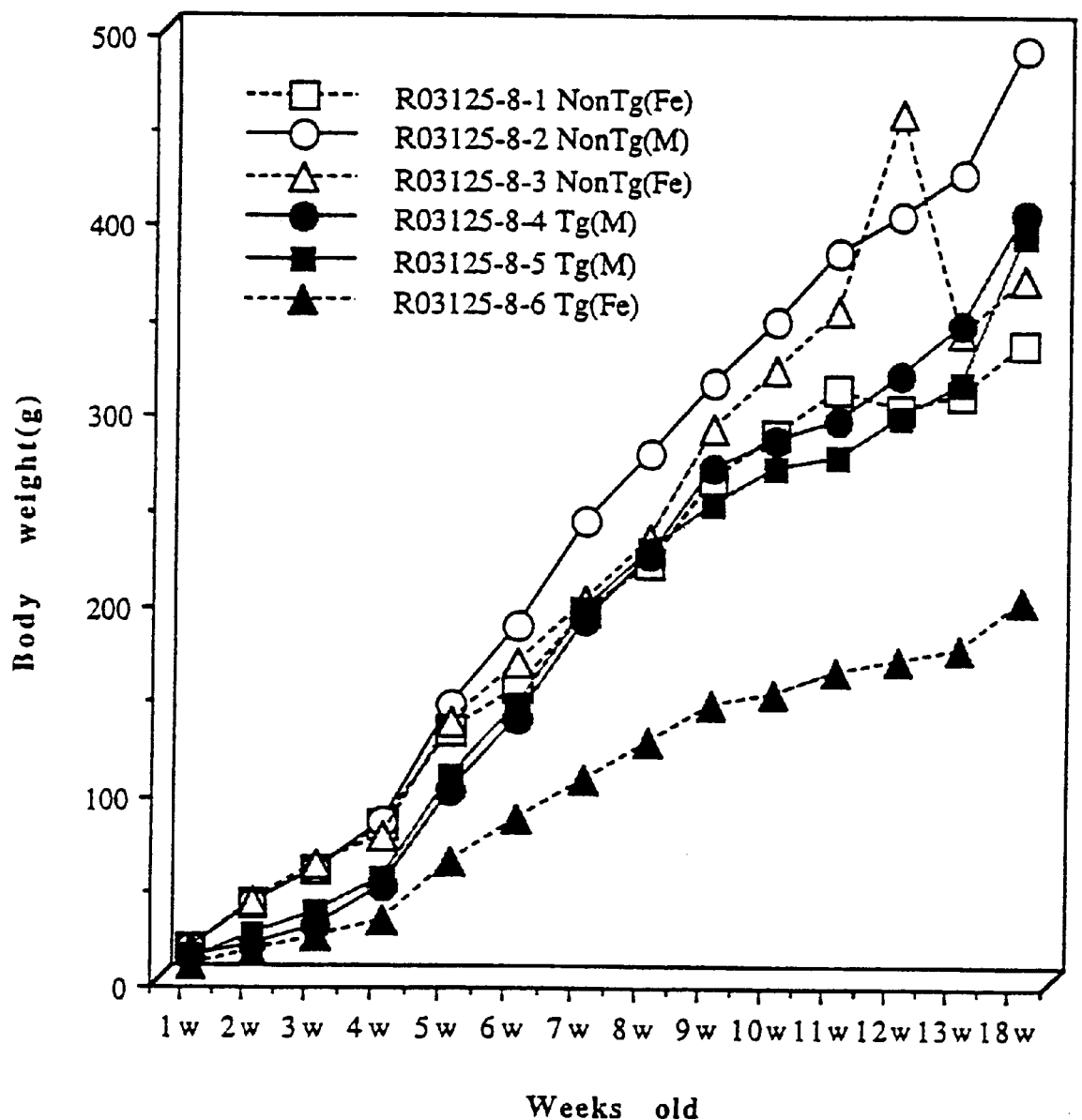
FIG. 13 shows the results of body weight-weighing of the transgenic rat RO3125-8F1 line conducted in Example 3.

In the present invention, the proteins belonging to monocyte chemoattractant protein family include a protein which is capable of binding to C-C chemokine receptor type-2 and has monocyte chemoattractant activity or a receptor thereof. These include MCP-1, MCP-2, MCP-3, MCP-4 or MCP-5 as such a protein, or a receptor thereof.

The transgenic animal of the present invention is created by introducing a desired monocyte chemoattractant protein gene and/or the corresponding receptor gene into an unfertilized egg, a fertilized egg, a spermatozoon, a germinal cell containing a primordial germinal cell thereof, or the like, preferably in the embryogenic stage in the development of a non-human mammal (more preferably in the single-cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to introduce a desired monocyte chemoattractant protein gene and/or the corresponding receptor gene into a somatic cell, a living organ, a tissue cell, or the like, by gene transformation methods, and utilize it for cell culture, tissue culture etc. Furthermore, these cells may be fused with the above-described germinal cell by a commonly known cell fusion method to create a transgenic animal.

"Non-human mammals" that can serve as the subject of the present invention include bovines, pigs, sheep, goat, rabbits, dogs, cats, guinea pigs, hamsters, rats and mice. Above all, rabbits, dogs, cats, guinea pigs, hamsters or rats, especially rats (Wistar, SD etc.), and in particular Wistar rats, are the most preferable subject animals for disease models.

"Mammals" that can serve as the subject of the present invention include humans, as well as the above-mentioned "non-human mammals."

The exogenous mutant gene of monocyte chemoattractant protein gene in the present invention is exemplified by genes resulting from variations (e.g., mutations) in the DNA sequence of the original exogenous monocyte chemoattractant protein gene, including genes involving base addition, deletion, substitution with other bases etc. More specifically, it is preferable that said base addition, deletion, substitution with other bases result in 1 to 5 (preferably 1 or 2) amino acids substituted, added or deleted in the amino acid sequence constituting the monocyte chemoattractant protein.

The exogenous gene encoding monocyte chemoattractant protein or the corresponding receptor in the present invention may be derived from a mammal of the same species as, or a different species from, the non-human mammal as the subject of transformation or expression. In introducing a monocyte chemoattractant protein gene and/or the corresponding receptor gene into the subject animal, it is generally advantageous to use said gene as a gene construct wherein said gene is ligated downstream of a promoter capable of and operably linked to expressing said gene in the subject animal cells. Specifically, a transgenic non-human mammal showing high expression of the desired monocyte chemoattractant protein gene and/or the corresponding receptor gene can be created by microinjecting a vector ligated with said gene into a fertilized egg of the subject non-human mammal (e.g., rat fertilized egg) downstream of various promoters capable of expressing the monocyte chemoattractant protein and/or the corresponding receptor derived from various mammals (rabbits, dogs, cats, guinea pigs, hamsters, rats, mice etc., preferably rats etc.) having a monocyte chemoattractant protein and/or the corresponding receptor gene highly homologous to the human monocyte chemoattractant protein gene and/or the corresponding receptor gene. Useful monocyte chemoattractant protein and/or the corresponding receptor gene expression vectors include *Escherichia coli*-derived plasmids, *Bacillus subtilis*-derived plasmids, yeast-derived plasmids, bacteriophages such as λ phage, retroviruses such as Moloney leukemia virus, and animal viruses such as vaccinia virus or baculovirus. Of these vectors, *Escherichia coli*-derived plasmids, *Bacillus subtilis*-derived plasmids, yeast-derived plasmids etc. are preferably used, with greater preference given to *Escherichia coli*-derived plasmids.

Useful promoters for such gene expression regulation include, for example, promoters for genes derived from viruses (cytomegalovirus, Moloney leukemia virus, JC virus, breast cancer virus etc.), and promoters for genes derived from various mammals (humans, rabbits, dogs, cats, guinea pigs, hamsters, rats, mice etc.) and birds (chickens etc.) [e.g., genes for albumin, insulin II, erythropoietin, endothelin, osteocalcin, muscular creatine kinase, platelet-derived growth factor β, keratins K1, K10 and K14, collagen types I and II, atrial natriuretic factor, dopamine β-hydroxylase, endothelial receptor tyrosine kinase (generally abbreviated Tie2), sodium-potassium adenosine triphosphorylase (generally abbreviated Na,K-ATPase), neurofilament light chain, metallothioneins I and IIA, metalloproteinase I tissue inhibitor, MHC class I antigen (generally abbreviated H-2L), smooth muscle α actin, polypeptide chain elongation factor 1α (BF-1α), β actin, α and β myosin heavy chains, myosin light chains 1 and 2, myelin base protein, serum amyloid component, myoglobin, renin etc.], preferably cytomegalovirus promoters, human and chicken β actin promoters etc., with greater preference given to using cytomegalovirus promoters.

It is preferable that the above-mentioned vectors have a sequence for terminating the transcription of the desired messenger RNA in the transgenic animal (generally referred to as terminator); for example, gene expression can be manipulated using a sequence with such function contained in various genes derived from viruses, mammals and birds. Preferably, the simian virus SV40 terminator etc. are commonly used. Additionally, for the purpose of increasing the expression of the desired gene, the splicing signal and enhancer region of each gene, a portion of the intron of a eukaryotic organism gene may be ligated 5' upstream of the promoter region, or between the promoter region and the translational region, or 3' downstream of the translational region as desired.

The translational region for a monocyte chemoattractant protein or the corresponding receptor can be obtained using the entire or portion of genomic DNA of blood, kidney or fibroblast origin from various mammals (humans, rabbits, dogs, cats, guinea pigs, hamsters, rats, mice etc.) or of various commercially available genomic DNA libraries, as a starting material, or using complementary DNA prepared by a known method from RNA of blood, kidney or fibroblast origin as a starting material. Also, an exogenous gene of human monocyte chemoattractant protein or the corresponding receptor can be obtained using complementary DNA prepared by a known method from RNA of human fibroblast origin as a starting material. Alternatively, the translational region for a monocyte chemoattractant protein or the corresponding receptor obtained by the above-mentioned cell or tissue can be made variant by point mutagenesis etc. All these translational regions can be utilized in transgenic animals.

To obtain said translational region, it is possible to prepare DNA incorporating an exogenous gene encoding monocyte chemoattractant protein or the corresponding receptor engineering technique in which said gene is ligated downstream of the above-mentioned promoter (preferably upstream of the translation termination site) as a gene construct capable of being expressed in the transgenic animal.

Monocyte chemoattractant protein gene and/or the corresponding receptor gene is introduced at the fertilized egg cell stage in a manner such that the gene is present in excess in all the germinal cells and somatic cells of the subject non-human mammal. The fact that a monocyte chemoattractant protein gene or the corresponding receptor gene is present in excess in the germinal cells of the animal created by gene introduction means that all offspring of the created animal will have the monocyte chemoattractant protein gene and/or the corresponding receptor gene in excess in all of the germinal cells and somatic cells thereof. The animal's offspring that inherits the gene also have the monocyte chemoattractant protein and/or the corresponding receptor in excess in all of the germinal cells and somatic cells thereof. By obtaining a homozygotic animal having the introduced gene in both sets of homologous chromosomes thereof, and mating a male and female of the animal, all offspring can be confirmed as stably retaining said gene and having said gene in excess, and can then continuously propagated in ordinary rearing circumstances. These animals will phenotypically display excess monocyte chemoattractant protein and/or the corresponding receptor.

The fertilized egg used to introduce an exogenous gene (e.g., exogenous genes encoding monocyte chemoattractant protein or receptor thereof), uses a gene (preferably an intron-free gene) differing from any of the endogenous genes possessed by the subject animal. The gene is introduced into a fertilized egg of the subject non-human mammal (preferably a rat etc., more preferably a Wistar rat etc.) or an ancestor thereof, where the fertilized egg is obtained by mating a male non-human mammal of the same species (preferably a male rat etc., more preferably a male Wistar rat etc.) and a female non-human mammal of the same species (preferably a female rat etc., more preferably a female Wistar rat etc.).

Although a fertilized egg can be obtained by spontaneous mating, preference is given to the method in which the estrous cycle of a female non-human mammal (preferably a female rat etc., more preferably a female Wistar rat etc.) is artificially controlled, after which the female is mated with a male non-human mammal (preferably a male rat etc., more preferably a male Wistar rat etc.). Although the method of artificially controlling the estrous cycle of a female non-human mammal is preferably exemplified by one in which follicle-stimulating hormone (pregnant mare's serum gonadotropin, generally abbreviated PMSG) and then luteinizing hormone (human chorionic gonadotropin, generally abbreviated hCG) are administered by, for example, intraperitoneal injection, preferred hormone doses and dosing intervals vary depending on the species of the non-human mammal. Also, when the Wistar rat is used, the animal is preferably one aged 8 weeks or more that has been reared with daily lighting of about 12 hours (e.g., 7:00–19:00) for about 1 week. When the non-human mammal used is a female rat (preferably a female Wistar rat), preference is normally given to the method in which a fertilized egg is obtained by crossing the female rat receiving follicle-stimulating hormone and then luteinizing hormone administered after about 48 hours, with a male rat; the follicle-stimulating hormone dose is normally about 20 to about 50 IU/animal, preferably about 30 IU/animal, and the luteinizing hormone dose is normally about 0 to about 10 IU/animal, preferably about 5 IU/animal.

After an exogenous gene (for example, an exogenous monocyte chemoattractant protein and/or a gene of receptor thereof) is introduced into the thus-obtained fertilized egg by the above-described method, a female non-human mammal having DNA incorporating an exogenous gene (preferably an exogenous monocyte chemotactic and activating factor gene) artificially transplanted and implanted therein is obtained.

Preference is given to the method in which the fertilized egg obtained is artificially transplanted and implanted in a false pregnant female non-human mammal in which fertility was induced by mating with a male non-human mammal after administration of luteinizing hormone-releasing hormone (generally abbreviated LHRH) or an analogue thereof.

The dose of LHRH or an analogue thereof and the timing of mating with a male non-human mammal after its administration vary depending on the species of the non-human mammal. When the non-human mammal is a female rat (preferably a female Wistar rat), it is preferably crossed with a male rat at about 4 days after administration of LHRH or an analogue thereof ((e.g., [3,5-Dil-Tyr$^5$]-LH-RH, [Gln$^8$]-LH-RH, [D-Ala$^6$]-LH-RH, des-Gly$^{10}$, [D-His(Bzl)$^6$]-LH-RH) ethylamide), the dose of LHRH or an analogue thereof being normally about 10 to 60 μg/animal, preferably about 40 μg/animal.

A non-human mammal having DNA incorporating a monocyte chemoattractant protein gene and/or the corresponding receptor gene has the gene(s) expressed to a high extent, and may eventually develop heart diseases (e.g., acute heart failure, chronic heart failure, myocarditis), respiratory diseases, joint diseases (e.g., articular rheumatism, osteoarthritis), kidney diseases (e.g., renal insufficiency, glomerular nephritis, IgA nephropathy), arteriosclerosis, psoriasis, hyperlipidemia, allergic diseases (e.g., asthma, allergic rhinitis, atopic dermatitis), bone diseases (e.g., osteoporosis, rickets, osteomalacia, hypocalcemia), blood diseases, cerebrovascular disorders, traumatic cerebral disorders, infectious diseases, dementia, chronic inflammatory diseases etc., as a result of promotion of the function of the endogenous monocyte chemoattractant protein gene and/or the corresponding receptor gene, and can be utilized as a pathologic model animal for these diseases. Specifically, using the transgenic animal of the present invention, it is possible to elucidate the mechanism of pathogenesis of these diseases, to determine therapies, and to screen for candidate compounds for the purpose of research and development of therapeutic drugs. In such cases, it is likely that other functions of the monocyte chemoattractant protein gene and/or the corresponding receptor gene in vivo will be elucidated; the transgenic animal of the present invention is also expected to serve as an experimental model for the elucidation of the mechanism of such mechanisms.

A non-human mammal having DNA incorporating an exogenous monocyte chemoattractant protein gene and/or the corresponding receptor thereof, or a mutant gene thereof downstream of the cytomegalovirus promoter, in particular, exhibits body weight gain suppression, eyelid thickening etc., and can be utilized as a pathologic model animal for chronic inflammatory diseases, allergic diseases (e.g., asthma, allergic rhinitis, atopic dermatitis) etc.

Furthermore, utilizing a vector incorporating a monocyte chemoattractant protein gene and/or the corresponding receptor gene would enable gene therapy for those diseases caused by these genes deficiency.

Other potential applications of the above-described transgenic animal include:

① use as a cell source for tissue culture,

② elucidation of the association of the complex action of intranuclear receptors and transcription factors by direct analysis of DNA or RNA in tissue of the transgenic mouse of the present invention or by analysis of protein tissue expressed by the gene, ③ research into the function of cells derived from tissues that are usually difficult to culture, e.g., smooth muscle cells, using cells of tissue having the gene cultured by a standard tissue culture technique, ④ screening for a drug that enhances cell function using the cells described in term ③ above, and ⑤ isolation and purification of a monocyte chemoattractant protein and/or a receptor thereof expressed to high extent and preparation of an antibody directed thereto.

Animals having abnormalities due to overexpression of a monocyte chemoattractant protein were successfully created from the monocyte chemoattractant protein gene genetransformed non-human mammal of the present invention.

Animals showing overexpression of a monocyte chemoattractant protein receptor were successfully created from the monocyte chemoattractant protein receptor introduced non-human mammal of the present invention. Animals showing overexpression of both the monocyte chemoattractant protein gene and monocyte chemoattractant protein receptor gene were successfully created from the both gene-introduced non-human mammal of the present invention, and showed human type monocyte chemotaxis.

These animals may develop heart diseases, respiratory diseases, joint diseases, kidney diseases, arteriosclerosis, psoriasis, hyperlipidemia, allergic diseases, bone diseases, blood diseases, cerebrovascular disorders, traumatic cerebral disorders, infectious diseases, dementia, chronic inflammatory diseases etc., and can be utilized as pathologic model animals for these diseases. For example, using the rat of the present invention, it is possible to elucidate the mechanism of pathogenesis of these diseases and to determine therapies for these diseases.

The above-described transgenic animals of the present invention can be utilized for the purpose of supplying cells showing high expression of a monocyte chemoattractant protein gene, a monocyte chemoattractant receptor protein gene or both, and elucidating the signal transmission mechanism of chemokines and receptors thereof.

Modes of Embodiment of the Invention

The present invention is hereinafter described in more detail by means of the following examples, which are not to be construed as limitative.

EXAMPLES

Example 1

1) Cloning of the Rat Monocyte Chemoattractant Protein Gene

From the base sequence of the rat monocyte chemoattractant protein-1 (RatMCP-1 ) cDNA described by Yoshimura et al. (Biochem. Biophys. Res. Commun., Vol. 174, p. 504, 1991), a 27-mer primer 1 (5'-CTTGTCGACATGCAGGTCTCTGTCACG-3'; SEQ ID NO:1) and a 28-mer primer 2 (5'-CTTGTCGACACTAGTTCTCTGTCATACT-3'; SEQ ID NO:2) were prepared. Subsequently, a reaction liquid was prepared by a conventional method using a rat macrophage 5'-stretch cDNA library (produced by Clontech) as a starting material, after which a polymerase chain reaction (PCR) was carried out under conditions such that the reaction liquid was reacted at 94° C. for 3 minutes, 55° C. for 2 minutes and 72° C. for 3 minutes, then reacted at 94° C. for 1 minute, 55° C. for 1 minute and 72° C. for 3 minutes in 35 cycles, and finally reacted at 94° C. for 1 minute, 55° C. for 1 minute and 72° C. for 10 minutes, followed by overnight storage at 4° C. Subsequently, the base sequence was determined by a conventional method using a DNA sequencer (produced by Perkin-Elmer), and was identified as a known library Rat MCP-1 cDNA. Next, the above Rat MCP-1 cDNA and the plasmid pAKKO-111H (Hinuma, S. et al., Biochim. Biophys. Acta., Vol. 1219, p. 251, 1994) were cleaved with restriction enzyme SalI; the resulting rat MCP-1 cDNA fragment and pAKKO-111H fragment (4.5 kbp) were treated at 16° C. for 60 minutes using a Takara ligation kit (produced by Takara Shuzo Co., Ltd.), after which they were ligated; *Escherichia coli* JM109 (produced by Nippon Gene) was transformed using this reaction liquid to yield an ampicillin-resistant (Ampr) strain. From this transformant (*Escherichia coli* JM109/p), plasmid DNA was recovered, followed by base sequencing by a conventional method, to confirm that the rat MCP-1 cDNA fragment was ligated into pAKKO-111H, and obtain the plasmid pAKKO-111-RatMCP-1 (4.9 kbp). Examination of this gene construct by multiple restriction enzyme cleavage demonstrated the absence of detectable translocations.

2) Construction of the Plasmid pBK-CMV-RatMCP-1 Having the Rat Monocyte Chemotactic and Activating Factor Gene Downstream of the Cytomegalovirus Gene Regulation Region The cytomegalovirus (CMV) promoter used was a commercially available plasmid PBK-CMV (produced by STRATAGENE).

First, pAKKO-111-RatMCP-1 as obtained in term (1) above was cleaved with restriction enzyme SalI; 100 ng of the resulting 400 bp cDNA-containing fragment was subjected to 5'-terminal dephosphorylation with calf small intestine alkaline phosphatase (produced by Takara Shuzo Co., Ltd.). Next, the multi-cloning site (MCS) inserted in the LacZ of commercially available pBK-CMV was cleaved with restriction enzyme SalI; the above pAKKO-111SalI fragment (400 bp) and the resulting pBK-CMV fragment (4.5 kbp) were treated at 16° C. for 60 minutes using a Takara ligation kit (produced by Takara Shuzo Co., Ltd.) to ligate them; *Escherichia coli* JM109 (produced by Nippon Gene) was transformed using this reaction liquid to yield a neomycin-resistant strain (Neor). Plasmid DNA was recovered from this transformant (*Escherichia coli* JM109/p) and subjected to restriction enzyme cleavage to confirm that the pAKKO-111SalI fragment was ligated into the pBK-CMV fragment in the orthodox orientation, and obtain the plasmid pBK-CMV-RatMCP-1 (4.9 kbp). The construction scheme for this plasmid is shown in FIG. 1. Examination of this gene construct by multiple restriction enzyme cleavage demonstrated the absence of detectable translocations.

3) Creation of Transgenic Rats Containing a Rat MCP-1 Gene Fusion Complex Downstream of the Cytomegalovirus Gene Regulation Region For egg collection, Wistar rats were purchased at 8 weeks of age and reared with daily lighting of 12 hours (7:00–19:00) for 1 week. First, at 11:00 of Day 1, follicle-stimulating hormone (pregnant mare's serum gonadotropin, generally abbreviated PMSG) (30 IU/animal) was intraperitoneally injected; at 11:00 of Day 3, luteinizing hormone (human chorionic gonadotropin, generally abbreviated hCG) (5 IU/animal) was intraperitoneally injected. At 17:00, these rats were mated and crossed with male Wistar rats aged 10 weeks or more in a 1:1 ratio. At 9:00 of Day 4, the crossed female rats were examined for the presence of a vaginal plug. Starting at 13:30, the animals found to have a vaginal plug were killed for egg collection. Fertilized eggs with pronucleus formation were selected; starting at 14:30, the plasmid pBK-CMV-RatMCP-1 as obtained in paragraph 2) above was cleaved with ApaLI and MluI, and prepared to 10 μg to 100 μg/ml concentrations; a 1 to 2 μl portion was injected into the male pronucleus of each fertilized Wistar rat egg in the single-cell phase, under a microscope. Subsequently, the egg cell was cultured in commonly known HER medium; after a 2-cell embryo was confirmed at 13:30 of Day 5, the egg was transplanted to the oviduct of a false pregnant female Wistar rat for implantation by the method described by Wagner et al. (Proc. Nat. Acad. Sc. U.S.A., Vol. 78, p. 5016, 1981). False pregnant female Wistar rats (11 weeks or more of age) were given subcutaneous injection of LHRH (40 μg/animal) at 13:00 of Day 0; at 17:00 of Day 4, they were mated and crossed with male Zucker lean rats aged 12 weeks or more in a 1:1 ratio. At 9:00 of Day 5, the crossed female rats were examined for the presence of a vaginal plug; those found to have a vaginal plug were used for the above-described purpose.

4) Gene Expression Analysis of a Rat Monocyte Chemoattractant Protein-1 Gene-Transformed Rat Analyte RNA was extracted from portions of the brain, heart, liver, lung, kidney, spleen, testis and eyelid tissues of the above-described transgenic rat (animal No. RO3125-8) and a control rat via tissue disruption in guanidine by a conventional method. The nucleic acid pellets thus obtained were once washed in 70% ethanol, dried, and re-suspended in sterile water.

Using the above-described primers (SEQ ID NO:3 and SEQ ID NO:4) and the RT-PCR plus kit (Toyobo), a reverse transpolymerase chain reaction (RT-PCR) was conducted. Using 20 μg of the RNA preparation as a substrate, the reaction product was first treated with reverse transcriptase at 60° C. for 30 minutes, then at 94° C. for 2 minutes, followed by the addition of Taq polymerase, after which a reaction was carried out in 40 cycles of heating at 94° C. for 1 minute and 60° C. for 1.5 minutes, followed by a treatment at 60° C. for 7 minutes; the reaction product was subjected to electrophoresis through 1.0% agarose GTG (produced by FMC Bioproducts) gel.

As a result, expression of both transfected genes was observed in all organs of the transgenic rat analyzed (animal No. RO3125-8).

Example 2

1) Gene Analysis of Transgenic Rats

Using the DNA collected from the tails of offspring at 3 weeks of age, gene analysis was conducted by the polymerase chain reaction method. Specifically, using the 20-mer primer 3 (5'-CGGCTCGTATATTGTGTGGA-3'; SEQ ID NO:3) in rat MCP-1 cDNA and the 22-mer primer 4 (5'-CTTCAGATTTATGGGTCAAGTT-3'; SEQ ID NO:4) in the rat MCP-1 cDNA, a polymerase chain reaction (PCR) was carried out. Analysis of a total of 181 baby rats revealed 12 PCR-positive or false-positive rats.

TABLE 1

Results of Creation of Transgenic Rats by Injection of the Rat MCP-1 DNA

| | | Number of Rats | | |
|---|---|---|---|---|
| Gene | Experiment No. | Number of Embryos Transplanted | Number of Babies | Number of PCR-tested Animals | Number of PCR-positive Animals |
| CMV-rMCP-1 | 53 | 79 | 24 | 24 | 2 |
| | 54 | 79 | 56 | 56 | 2 |
| | 55 | 89 | 31 | 31 | 4 |
| | 56 | 73 | 41 | 41 | 4 |
| | 57 | 28 | 10 | 10 | 0 |
| | 58 | 69 | 19 | 19 | 0 |
| | Total | 417 | 181 | 181 | 12 |

These 12 PCR-positive or false-positive animals were analyzed by the Southern hybridization method using tail DNA preparations, with a digoxigenin-DNA probe (labeled by the commonly known riboprobe method) containing the rat MCP-1 gene sequence. For each case, the DNA from the tail was cleaved with NdeI and MluI, and tested with a fragment purified from a rat MCP-1 gene fusion complex (FIG. 1), previously labeled with digoxigenin, as a probe. Labeling was achieved using a commercially available DIG luminescent detection kit (produced by Boehringer Mannheim). Analyte DNA was extracted from an about 1 cm cut of the tail by the method described by Hogan, B. et al. (Manipulating the Mouse Embryo, published by Cold Spring Harbor Laboratory, 1986). The nucleic acid pellets thus obtained were once washed in 70% ethanol, dried, and re-suspended in 200 μl of 10 mM Tris (pH 8.0) and 1 mM EDTA. One microliter of the tail DNA preparation was 50-fold diluted with sterile water; using primers 1 and 2, a reaction was carried out in 30 cycles of heating at 94° C. for 30 seconds, 60° C. for 1 minute and 72° C. for 1 minute; the reaction product was subjected to electrophoresis through 1.2% agarose GTG (produced by FMC Bioproducts) gel; rats showing a DNA band of 509 bp size were selected. Of the 181 live-born babies, 12 showed a DNA band of 509 bp size. Furthermore, 10 μg of the DNA of each of these 12 PCR-positive or false-positive animals was completely cleaved with restriction enzymes NdeI and MluI, subjected to electrophoresis through 1.0% agarose gel, and transferred onto a nylon filter by the method described by Southern (Journal of Molecular Biology, Vol. 98, p. 503, 1975). This filter was hybridized to the probes overnight, twice washed with 2×SSC and 0.1% SDS at room temperature, then twice washed with 0.1×SSC and 0.1% SDS at 68° C. Since this Southern hybridization resulted in a signal at the 1.7 kbp position in 8 of the 12 animals examined, it was demonstrated that these 8 retained the injected rat MCP-1 gene.

Southern hybridization of 12 PCR-positive animals confirmed the introduction of the rat MCP-1 gene in 8 animals. From these results, 8 animals, namely RO3056-2 (male), RO3073-7 (female), RO3124-4 (female), RO3125-4 (male), RO3125-8 (female), RO3142-2 (male), RO3142-12 (female) and RO3143-5 (male), were confirmed as transgenic rats (FIG. 4).

Example 3

1) Body Weight Change Rat MCP-1 Gene-Transformed Rats

CMV-MCP-1 gene-transformed RO3125-8 rats (F0 generation) were regularly weighed until 22 weeks of age. As a result, the RO3125-8 rats were found to be lighter than the other rats of the same litter, which tended to gain weight with age, and to show no such tendency. Body weight gain suppression was noted in RO3125-8; slight body weight gain suppression was noted in RO3073-7. However, the weight change in each of RO3056-2, RO3124-4, RO3125-4, RO3142-2, RO3142-12 and RO3143-5 showed the same tendency as that in the other rats of the same litter, demonstrating no explicit difference. Males (RO3056-2, RO3125-4, RO3142-2, RO3143-5) of these transgenic rats were respectively mated with 2 normal female Wistar rats (8 weeks of age) for crossing. As a result, babies of each transgenic rat were obtained. Females (RO3073-7, RO3124-4, RO3125-8, RO3142-12) of these transgenic rats were respectively mated with 1 normal male Wistar rat (11 weeks of age) for crossing. As a result, babies of each transgenic rat were obtained. From the tails of these babies at 3 weeks of age, DNA was collected and subjected to a polymerase chain reaction (PCR) using the above-described primer 3 (5'-CGGCTCGTATATTGTGTGGA-3'; SEQ ID NO:3) and primer 4 (5'-CTTCAGATTTATGGGTCAAGTT-3'; SEQ ID NO:4), followed by identification of transgenic rats.

Of these transgenic rats, those obtained from RO3125-8 (F1 generation) were regularly weighed in the same manner as above until 6 weeks of age. Of these transgenic rats, RO3125-8-6 (female) was an animal showing marked body weight gain suppression. RO3125-8-4 and RO3125-8-4 (males) were animals with slightly less body weight gain suppression (FIGS. 5 through 13).

2) Obtainment of Aberrant Animals

Figure 14A:
FIG. 14A shows the aberrant individual of the transgenic rat RO3125-8F1 line obtained by Example 3.
Figure 14B:
FIG. 14B shows a non-transgenic rat.

In 1 of the 3 F1 generation babies born in the first delivery by transgenic rats obtained from the transgenic rat RO3125-8 (F0 generation), which showed body weight gain suppression, by mating in the same manner as the method described in term 1) above, marked body weight gain suppression was noted. This animal showed thickening of both eyelids and adhesion of accessory lacrimal gland secretion even after weaning. Another 1 animal showed eyelid thickening (both eyes) and accessory lacrimal gland secretion adhesion. Also, of the 3 gene-transformed rats born in the second delivery, obtained by mating in the same manner as above, 1 died at 2 weeks of age. The other 2 gene-transformed rats showed body weight gain suppression, eyelid thickening and secretion adhesion (FIG. 14).

Example 4

1) Cloning of the Human Monocyte Chemoattractant Protein (hMCP-1) Gene

For the purpose of isolating hMCP-1 cDNA, a commercially available LPS-stimulated human monocyte λgt10 cDNA library (produced by Clontech) was proliferated in *Escherichia coli* C600; based on the cDNA obtained, a 19-mer primer 5 (5'-CTCTCGCCTCCAGCATGAA-3'; SEQ ID NO:5) in hMCP-1 cDNA, and a 20-mer primer 6 (5'-AAGACCCTCAAAACATCCCA-3'; SEQ ID NO:6) in the same rat MCP-1 cDNA were prepared, using which primers a polymerase chain reaction (PCR) was carried out. As a result, a 577 bp PCR product was obtained, which was ligated with a fragment obtained by cleaving the plasmid pCR II (3.9 kbp) in a PCR direct cloning kit (produced by Invitrogen) with restriction enzymes SacI and NotI. Using this reaction liquid, *Escherichia coli* JM109 (produced by Nippon Gene) was transformed to yield an ampicillin-resistant strain. Plasmid DNA was recovered from this transformant (*Escherichia coli* JM109/p) and subjected to restriction enzyme cleavage to confirm that hMCP-1 was ligated into the pCRII fragment, and obtain the plasmid pCRII-hMCP-1 (4.5 kbp). Determination of its base sequence by a conventional method using a DNA sequencer (produced by Perkin-Elmer) confirmed identity as human monocyte chemotactic and activating factor cDNA.

Figure 15:
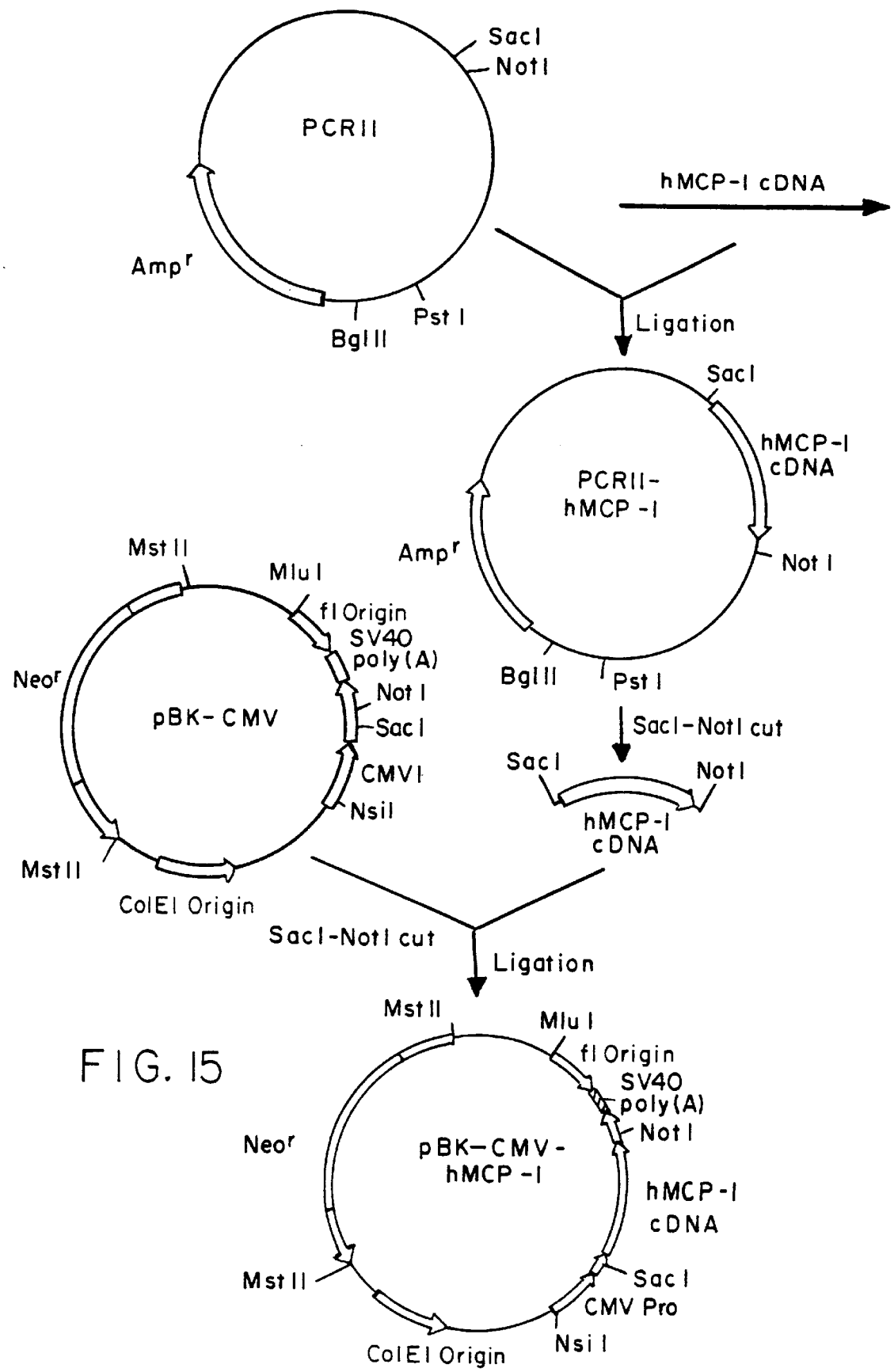
FIG. 15 shows the construction scheme of plasmid pBK-CMV-hMCP-1 constructed by Example 4.
Figure 16:
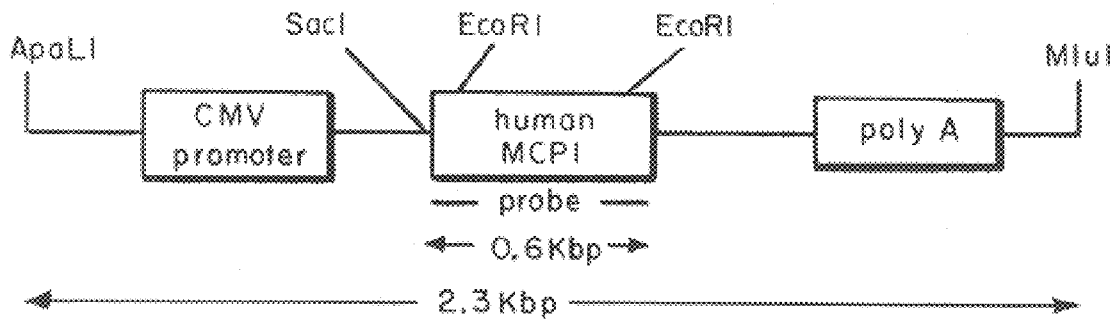
FIG. 16 shows the structure of a gene into which human MCP-1 is incorporated downstream of and operably linked to a CMV promoter.

2) Construction of the Plasmid pBK-CMV-hMCP-1 Having the hMCP-1 Gene Downstream of the Cytomegalovirus Gene Regulation Region First, pCRII-hMCP-1 (4.5 kbp) was cleaved with restriction enzymes SacI and NotI. Separately, the multi-cloning site inserted in the plasmid pBK-CMV was cleaved with restriction enzymes SacI and NotI; the pBK-CMV fragment (4.5 kbp) and the hMCP-1 fragment (600 bp) were treated at 16° C. for 60 minutes using a Takara ligation kit (produced by Takara Shuzo Co., Ltd.) to ligate them; *Escherichia coli* JM109 (produced by Nippon Gene) was transformed using this reaction liquid to yield a neomycin-resistant strain. Plasmid DNA was recovered from this transformant (*Escherichia coli* JM109/p) and subjected to restriction enzyme cleavage with SacI to confirm that the hMCP-1 fragment was ligated into the pBK-CMV fragment, and obtain the plasmid pBK-CMV-hMCP-1 (5.1 kbp). The construction scheme for this plasmid is shown in FIG. 15. Examination of this gene construct by multiple restriction enzyme cleavage demonstrated the absence of detectable translocations.

Example 5

1) Creation of Transgenic Rats Containing a hMCP-1 Gene Fusion Complex Downstream of the Cytomegalovirus Gene Regulation Region For egg collection, Wistar rats were purchased at 8 weeks of age and reared with daily lighting of 12 hours (7:00–19:00) for 1 week. First, at 11:00 of Day 1, follicle-stimulating hormone (pregnant mare's serum gonadotropin, generally abbreviated PMSG) (30 IU/animal) was intraperitoneally injected; at 11:00 of Day 3, luteinizing hormone (human chorionic gonadotropin, generally abbreviated hCG) (5 IU/animal) was intraperitoneally injected. At 17:00, these rats were mated and mated with male Wistar rats aged 10 weeks or more in a 1:1 ratio. At 9:00 of Day 4, the mated female rats were examined for the presence of a vaginal plug. Starting at 13:30, the animals found to have a vaginal plug were killed for egg collection. Fertilized eggs with pronucleus formation were selected; starting at 14:30, the plasmid pBK-CMV-hMCP-1 as obtained in Example 4 above was cleaved with ApaLI and MluI and prepared to 10 µg to 100 µg/ml concentrations; a 1 to 2 µl portion was injected into the male pronucleus of each fertilized Wistar rat egg in the single-cell phase under a microscope. The egg cell was cultured in HER medium; after a 2-cell stage embryo was confirmed at 13:30 of Day 5, the egg was transplanted to the oviduct of a false pregnant female Wistar rat for implantation by the method described by Wagner et al. (Proc. Nat. Acad. Sc. U.S.A., Vol. 78, p. 5016, 1981). False pregnant female Wistar rats (11 weeks or more of age) were given subcutaneous injection of LHRH (40 µg/animal) at 13:00 of Day 0; at 17:00 of Day 4, they were mated and crossed with male Zucker lean rats aged 12 weeks or more in a 1:1 ratio.

2) Gene Analysis of Transgenic Rats

Using the DNA collected from the tails of live-born babies at 3 weeks of age, gene analysis was conducted by the polymerase chain reaction method. Specifically, using the 21-mer primer 7 (5'-TTTCCAAGTCGCCACCCCATT-3';

SEQ ID NO:7) in human monocyte chemotactic and activating factor cDNA and the 21-mer primer 8 (5'-TTCTTTGGGACACTTGCTGCT-3'; SEQ ID NO:8) in the hMCP-1 cDNA, a polymerase chain reaction (PCR) was carried out. These 8 PCR-positive animals were analyzed by the Southern hybridization method using NotI-cleaved tail DNA preparations, with a digoxigenin-RNA probe (labeled by the riboprobe method) containing the hMCP-1 gene sequence. For each case, the DNA from the tail was cleaved with NotI and subjected to electrophoresis. An RNA probe prepared using the T3 sequence contained in the fragment [human monocyte chemoattractant protein-1 gene fusion complex (pBK-CMV-hMCP-1 )] recovered after electrophoresis (FIG. 15) as a primer was used after labeling with digoxigenin. Labeling was achieved using a commercially available DIG luminescent detection kit (produced by Boehringer Mannheim). Analyte DNA was extracted from an about 1 cm cut of the tail by the method described by Hogan et al. (Manipulating the Mouse Embryo, published by Cold Spring Harbor Laboratory, 1986). The nucleic acid pellets thus obtained were once washed in 70% ethanol, dried, and re-suspended in 200 µl of 10 mM Tris (pH 8.0) and 1 mM EDTA. One microliter of the tail DNA preparation was 50-fold diluted with sterile water; using primers 7 and 8, a reaction was carried out in 30 cycles of heating at 94° C. for 30 seconds, 65° C. for 1 minute and 72° C. for 1 minute; the reaction product was subjected to electrophoresis through 1.2% agarose GTG (produced by FMC Bioproducts) gel; rats showing a DNA band of 594 bp size were selected. Of the 8 live-born babies, 5 showed a DNA band of 594 bp size.

TABLE 2

Results of Creation of Transgenic Rats
by Injection of the Human Monocyte Chemoattractant Protein-1 Gene

| Gene | Experiment No. | Number of Embryos Transplanted | Number of Babies | Number of PCR-tested Animals | Number of PCR-positive Animals |
|---|---|---|---|---|---|
| CMV-hMCP-1 | 59 | 57 | 31 | 30 | 1 |
| | 60 | 75 | 26 | 26 | 1 |
| | 61 | 44 | 15 | 15 | 1 |
| | 62 | 54 | 27 | 27 | 3 |
| | 63 | 75 | 23 | 23 | 2 |
| | 64 | 49 | 20 | 20 | |
| | Total | 354 | 142 | 141 | 8 |

Furthermore, 10 µg of DNA of each of these 5 animals was completely cleaved with restriction enzymes ApaLI and MluI, subjected to electrophoresis through 1.0% agarose gel, and transferred onto a nylon filter by the method described by Southern (Journal of Molecular Biology, Vol. 98, p. 503, 1975). This filter was hybridized to the probe overnight, twice washed with 2×SSC and 0.1% SDS at room temperature, then twice washed with 0.1×SSC and 0.1% SDS at 68° C. Since this Southern hybridization resulted in a signal at 2.3 kbp position in the 5 animals examined, it was demonstrated that all these 5 retained the injected human monocyte chemotactic and activating factor gene.

Figure 17:
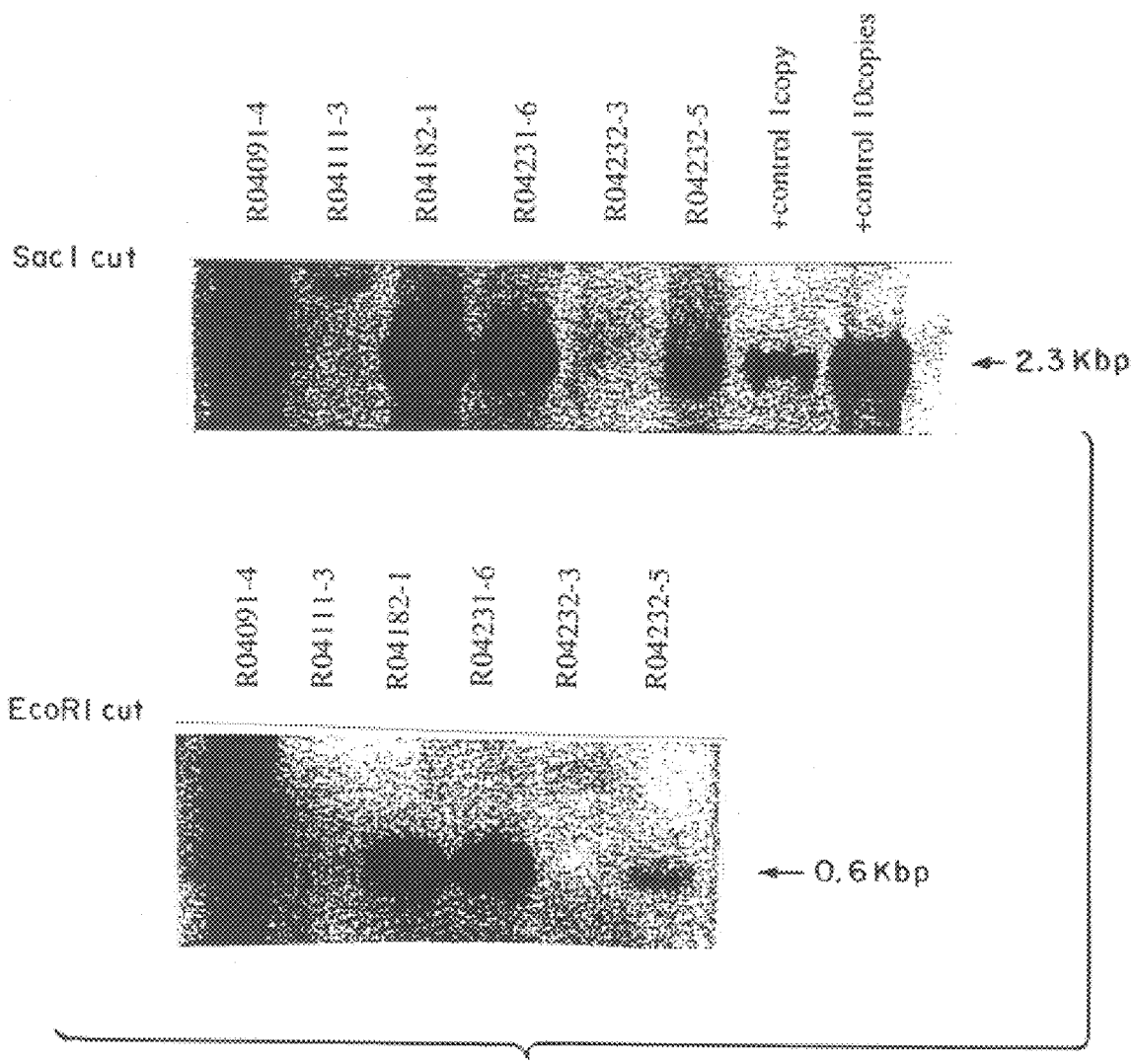
FIG. 17 shows the result of Southern hybridization (electrophoresis) conducted in Example 5.

Southern analysis for 5 PCR-positive animals confirmed the introduction of the human monocyte chemotactic and activating factor gene in all these animals. From these results, 5 animals, namely RO4091-4 (male), RO4182-1 (male), RO4231-6 (male), RO4232-5 (male) and RO5142-7 (female), were confirmed as gene-transfected rats (FIG. 17).

Example 6

1) Cloning of the Human Monocyte Chemoattractant Protein-1 Receptor Gene

From the base sequence of the rat monocyte chemoattractant protein-1 receptor cDNA described by Charo et al. (Proc. Nat. Acad. Sc. U.S.A., Vol. 91, p. 2752, 1994), a 33-mer primer (5'-ATCGTCGACATGCTGTCCACATCTCGTTCTCGG-3'; SEQ ID NO:9), which had a restriction enzyme SalI recognition sequence added, and a 33-mer primer (5'-CTCTCTAGATTATAAACCAGCCGAGACTTCCTG-3'; SEQ ID NO:10), which had a restriction enzyme XbaI recognition sequence in the rat monocyte chemoattractant protein-1 receptor cDNA, were prepared. Subsequently, a polymerase chain reaction (PCR) was conducted using a human cDNA library (produced by Clontech) as a starting material, after which the base sequence was determined by a conventional method using a DNA sequencer (produced by Perkin-Elmer), and was identified as a rat monocyte chemoattractant protein-1 receptor cDNA. Next, the plasmid pAKKO-111H was cleaved with restriction enzyme SalI; the above rat monocyte chemoattractant protein-1 receptor cDNA and the pAKKO-111H fragment (4.5 kbp) were treated at 15° C. overnight using a Takara ligation kit (produced by Takara Shuzo Co., Ltd.), to ligate them. Escherichia coli JM109 (produced by Nippon Gene) was transformed using this reaction liquid to yield an ampicillin-resistant strain. From this transformant (Escherichia coli JM109/p), plasmid DNA was recovered, followed by restriction enzyme cleavage, to confirm that the rat monocyte chemoattractant protein-1 cDNA fragment was ligated into pAKKO-111H, and obtain the plasmid pAKKO-111-hMCP-1 (5.6 kbp). Examination of this gene construct by multiple restriction enzyme cleavage demonstrated the absence of detectable translocations.

2) Construction of the Plasmid pBK-hMCP-1 R Having the Human Monocyte Chemoattractant Protein-1 Receptor (hMCP-1 R) Gene Downstream of the Cytomegalovirus Gene Regulation Region First, pAKKO-111-hMCP-1R (4.5 kbp) was cleaved with restriction enzymes SalI and BamHI; separately, the multiple cloning sites inserted in the plasmid pBK-CMV were cleaved with restriction enzymes SalI and BamHI; the resulting pBK-CMV fragment (4.5 kbp) and former fragment (1100 bp) were treated at 16° C. for 60 minutes using a Takara ligation kit (produced by Takara Shuzo Co., Ltd.), to ligate them. Escherichia coli JM109 (produced by Nippon Gene) was transformed using this reaction liquid to yield an ampicillin-resistant strain. From this transformant (Escherichia coli JM109/p), plasmid DNA was recovered, followed by restriction enzyme cleavage, to confirm that the hMCP-IR fragment was ligated into the pBK-CMV fragment in the orthodox orientation, and obtain the plasmid pBK-hMCP-1R (5.6 kbp). Examination of this gene construct by multiple restriction enzyme cleavage demonstrated the absence of detectable translocations.

Example 7

1) Creation of Transgenic Rats Containing a Human Monocyte Chemoattractant Protein-1 Gene Fusion Complex Downstream of the Cytomegalovirus Gene Regulation Region For egg collection, Wistar rats were purchased at 8 weeks of age and reared with daily lighting of 12 hours (7:00–19:00) for 1 week. First, at 11:00 of Day 1, follicle-stimulating hormone (pregnant mare's serum gonadotropin, generally abbreviated PMSG) (30 IU/animal) was intraperitoneally injected to these animals at 9 weeks of age, followed by rearing in the same manner as above; at 11:00 of Day 3, luteinizing hormone (human chorionic gonadotropin, generally abbreviated hCG) (5 IU/animal) was intraperitoneally injected. At 17:00, these rats were mated and crossed with male Wistar rats aged 10 weeks or more in a 1:1 ratio. At 9:00 of Day 4, the crossed female rats were examined for the presence of a vaginal plug. Starting at 13:30, the animals found to have a vaginal plug were killed for egg collection. Fertilized eggs with pronucleus formation were selected; starting at 14:30, the above-described plasmid pBK-hMCP-1R was cleaved with NaeI and ApaLI, and prepared to 10 μg to 100 μg/ml concentrations; a 1 to 2 μl portion was injected into the male pronucleus of each fertilized Wistar rat egg in the single-cell phase, under a microscope. Subsequently, the egg cell was cultured in HER medium; after a 2-cell embryo was confirmed at 13:30 of Day 5, the egg was transplanted to the oviduct of a false pregnant female Wistar rat for implantation by the method described by Wagner et al. (Proc. Nat. Acad. Sc. U.S.A., Vol. 78, p. 5016, 1981).

False pregnant female Wistar rats (11 weeks or more of age) were given subcutaneous injection of luteinizing hormone-releasing hormone (generally abbreviated LHRH) (40 μg/animal) at 13:00 of Day 0; at 17:00 of Day 4, they were mated and crossed with vasoligated male Zucker lean or Wistar rats aged 12 weeks or more in a 1:1 ratio. At 9:00 of Day 5, the crossed female rats were examined for the presence of a vaginal plug; those found to have a vaginal plug were used for the above-described purpose.

2) Gene Analysis of Transgenic Rats

Using the DNA collected from the tails of live-born babies at 3 weeks of age, gene analysis was conducted by the polymerase chain reaction method. Specifically, using a 22-mer primer (5'-CGGGGTCATTAGTTCATAGCCC-3'; SEQ ID NO:11) in a human monocyte chemoattractant protein-1 receptor cDNA and a 22-mer primer (5'-GACTCTCACTGCCCTATGCCTC-3'; SEQ ID NO:12) in the same receptor cDNA, a polymerase chain reaction (PCR) was carried out. Analysis of a total of 87 baby rats revealed 10 PCR-positive animals. These PCR-positive animals were further analyzed by the Southern hybridization method using tail DNA preparations cleaved with XbaI and BamHI, with a digoxigenin-DNA probe (labeled by the riboprobe method) containing the human monocyte chemoattractant protein-1 receptor gene sequence. For each case, the digoxigenin-labeled fragment purified from a human monocyte chemoattractant protein-1 receptor gene fusion complex (FIG. 15) was used as a probe. Labeling was achieved using a commercially available DIG luminescent detection kit (produced by Boehringer Mannheim). Analyte DNA was extracted from an about 1 cm cut of the tail by the method described by Hogan et al. (Manipulating the Mouse Embryo, published by Cold Spring Harbor Laboratory, 1986). The nucleic acid pellets obtained were once washed in 70% ethanol, dried, and re-suspended in 200 μl of 10 mM Tris (pH 8.0) and 1 mM EDTA. One microliter of the tail DNA preparation was 50-fold diluted with sterile water; using primer (SEQ ID NO:11) and primer (SEQ ID NO:12), a reaction was carried out in 25 cycles of heating at 94° C. for 30 seconds, 61° C. for 1 minute and 72° C. for 2 minutes; the reaction product was subjected to electrophoresis through 1.2% agarose GTG (produced by FMC Bioproducts) gel; rats showing a DNA band of 608 bp size were selected. Of the 87 live-born babies, 10 showed a DNA band of 608 bp size. Furthermore, 10 μg of the DNA of each of 7 of these 10 live animals was completely cleaved with restriction enzymes SalI and BamHI, subjected to electrophoresis through 1.0% agarose gel, and transferred onto a nylon filter by the method described by Southern (Journal of Molecular Biology, Vol. 98, p. 503, 1975). This filter was hybridized to the probes overnight, twice washed with 2×SSC and 0.1% SDS at room temperature, then twice washed with 0.1×SSC and 0.1% SDS at 68° C. Since this Southern hybridization resulted in a signal at 1.1 kbp position in the 7 animals examined, it was demonstrated that these 7 all retained the injected human monocyte chemotactic and activating receptor factor gene.

From these results, 7 animals, namely animal Nos. CM-02181F3 (female), CM-02251M1 (male), CM-02251M5 (male), CM-02251M7 (male), CM-02251F2 (female), CM-02251F7 (female) and CM-03041M1 (male), were confirmed as transgenic rats.

Example 8

Creation of Transgenic Rats Containing a Human Monocyte Chemoattractant Protein-1 Gene Fusion Complex and a Human Monocyte Chemattractant Protein-1 Receptor Gene Fusion Complex The transgenic rat described in Example 5, which contains a human monocyte chemoattractant protein-1 gene fusion complex, and the transgenic rat described in Example 7, which contains a human monocyte chemoattractant protein-1 receptor gene fusion complex, were crossed in 4 pairs to create transgenic rats containing both gene fusion complexes. Specifically, the 4 pairs comprised 1) human monocyte chemoattractant protein-1 receptor gene-transformed rat CM-02181F3 (female) and human monocyte chemoattractant protein-1 gene-transformed rat CM-04182M1 (male), 2) human monocyte chemotactic and activating factor receptor transgenic rat CM-02251F7 (female) and human monocyte chemoattractant protein-1 transgenic rat CM-04131M6 (male), 3) human monocyte chemoattractant protein-1 receptor gene-transformed rat CM-02251F2 (female) and human monocyte chemoattractant protein-1 gene-transformed rat CM-04232M5 (male), and 4) human monocyte chemoattractant protein-1 receptor gene-transformed rat CM-05142F7 (female) and human monocyte chemoattractant protein-1 gene-transformed rat CM-02251M1 (male).

As a result, 8 female and 7 male F1 animals were obtained from mating combination 1) on Jul. 12, 1997. Two female and 1 male F1 animals were obtained from crossing combination 2) on Jul. 8, 1997. Ten female F1 animals were obtained from crossing combination 3) on Jul. 11, 1997. One female and 2 male F1 animals were obtained from mating combination 4) on Jul. 12, 1997.

2) Gene Analysis of Transgenic Rats

Using the DNA collected from the tails of live-born babies at 3 weeks of age by the method described above, transfected genes were detected by the polymerase chain reaction method. Specifically, using the primer (SEQ ID NO:11) and primer (SEQ ID NO:12) in a human monocyte chemattractant protein-1 receptor cDNA and the primer (SEQ ID NO:7) and primer (SEQ ID NO:8) in a human monocyte chemoattractant protein-1 cDNA, a polymerase chain reaction (PCR) was carried out. Analysis of all baby rats revealed a total of 8 animals that were PCR-positive for both genes, consisting of 1 female and 2 males from mating combination 1), 1 female from mating combination 2), and 4 males from mating combination 3). No such animals were obtained from mating combination 4).

3) Gene Expression Analysis of Transgenic Rats

Analyte RNA was extracted from portions of the brain, heart, liver, lung, kidney, spleen and testis or ovary tissues of the above-described transgenic rats obtained from crossing combinations 1) and 3) and a control rat via tissue disruption in guanidine by a conventional method. The nucleic acid pellets obtained were once washed in 70% ethanol, dried, and re-suspended in sterile water.

Using primers (SEQ ID NO:7 and SEQ ID NO:8) and the RT-PCR plus kit (Toyobo), the reverse transpolymerase chain reaction method (RT-PCR) was conducted to examine human monocyte chemotactic and activating factor expression. Using 20 μg of the RNA preparation as a substrate, the reaction product was first treated with reverse transcriptase at 60° C. for 30 minutes, then at 94° C. for 2 minutes, followed by the addition of Taq polymerase, after which a reaction was carried out in 40 cycles of heating at 94° C. for 1 minute and 60° C. for 1.5 minutes, followed by a treatment at 60° C. for 7 minutes; the reaction product was subjected to electrophoresis through 1.0% agarose GTG (produced by FMC Bioproducts) gel. Using primers (SEQ ID NO:11 and SEQ ID NO:12) and the RT-PCR plus kit (Toyobo), the reverse transpolymerase chain reaction method (RT-PCR) was conducted to examine human monocyte chemoattractant protein-1 receptor expression. The experimental conditions used were the same as those shown above.

As a result, expression of both introduced genes was observed in all animals analyzed.

What we claim is:

1. A transgenic rat whose genome comprises a transgene comprising a DNA sequence encoding rat monocyte chemoattractant protein 1 operably linked to a cytomegalovirus promoter wherein said rat expresses said DNA sequence such that the said rat shows weight gain suppression or eyelid thickening compared to a rat whose genome does not comprise said transgene.

2. The transgenic rat of claim 1, which has eyelid thickening and which also shows adhesion of accessory lacrimal gland secretion compared with a rat whose genome does not comprise said transgene.

* * * * *

```
                        SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:1:

CTTGTCGACA TGCAGGTCTC TGTCACG                                        27

(2) INFORMATION FOR SEQ ID NO:2:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:2:

CTTGTCGACA CTAGTTCTCT GTCATACT                                       28

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:3:

CGGCTCGTAT ATTGTGTGGA                                                20

(2) INFORMATION FOR SEQ ID NO:4:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:4:
```

```
CTTCAGATTT ATGGGTCAAG TT                                              22

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

CTCTCGCCCT CCAGCATGAA                                                 20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

AAGACCCTCA AAACATCCCA                                                 20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

TTTCCAAGTC TCCACCCCAT                                                 20

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

TTCTTTGGGA CACTTGCTGC T                                               21

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

ATCGTCGACA TGCTGTCCAC ATCTCGTTCT CGG                                  33
```

```
(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

CTCTCTAGAT TATAAACCAG CCGAGACTTC CTG                                33

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

CGGGGTCATT AGTTCATAGC CC                                           22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

GACTCTCACT GCCCTATGCC TC                                           22
```